United States Patent
Younes

(10) Patent No.: US 9,386,952 B2
(45) Date of Patent: Jul. 12, 2016

(54) METHOD AND DEVICE(S) FOR DIAGNOSIS AND/OR TREATMENT OF SLEEP APNEA AND RELATED DISORDERS

(75) Inventor: Magdy Younes, Winnipeg (CA)

(73) Assignee: YRT LIMITED, Winnipeg, Manitoba (CA)

( * ) Notice: Subject to any disclaimer, the term of this patent is extended or adjusted under 35 U.S.C. 154(b) by 453 days.

(21) Appl. No.: 13/699,791

(22) PCT Filed: Jun. 8, 2011

(86) PCT No.: PCT/CA2011/000669
§ 371 (c)(1),
(2), (4) Date: Feb. 11, 2013

(87) PCT Pub. No.: WO2011/153622
PCT Pub. Date: Dec. 15, 2011

(65) Prior Publication Data
US 2014/0148720 A1    May 29, 2014

Related U.S. Application Data

(60) Provisional application No. 61/352,931, filed on Jun. 9, 2010.

(51) Int. Cl.
*A61B 5/08* (2006.01)
*A61B 5/00* (2006.01)
(Continued)

(52) U.S. Cl.
CPC .............. *A61B 5/4818* (2013.01); *A61B 5/08* (2013.01); *A61B 5/0816* (2013.01);
(Continued)

(58) Field of Classification Search
CPC .... A61B 5/08–5/0878; A61B 5/6804–5/6805; A61B 5/113–5/1135; A61B 5/4803–5/4818; A61B 5/6823; A61B 5/6831; A61H 9/0092; A61H 2201/0103; A61H 2205/08; A61H 2230/40–2230/425
USPC .................................................. 600/529–543
See application file for complete search history.

(56) References Cited

U.S. PATENT DOCUMENTS

| | | | | |
|---|---|---|---|---|
| 4,602,643 A | * | 7/1986 | Dietz | A61B 5/1135 600/534 |
| 5,277,194 A | * | 1/1994 | Hosterman | A61B 5/1135 600/534 |

(Continued)

FOREIGN PATENT DOCUMENTS

| WO | 02069878 A | 9/2002 |
|---|---|---|
| WO | 2009050702 A | 4/2009 |

OTHER PUBLICATIONS

Chinese Office Action for Chinese Patent Application No. 201180039296.2, with a mailing date of May 29, 2014 and English translation.

(Continued)

*Primary Examiner* — Catherine B Kuhlman
(74) *Attorney, Agent, or Firm* — Sim & McBurney

(57) ABSTRACT

Method and device for diagnosing and/or treating sleep apnea and related sleep disorders, such as snoring and respiratory effort-related arousals, includes an inflatable implement which is applied to the external surface of the chest and/or abdomen (Vest). Pressure is caused to rise to a predetermined positive value. The rate of airflow into and/or out of said Vest is monitored, whereby the Vest Flow is displayed or processed to obtain information about the breathing characteristics of the patient.

18 Claims, 23 Drawing Sheets

SYSTEM OVERVIEW

(51) Int. Cl.
*A61B 5/113* (2006.01)
*A61F 5/56* (2006.01)
*A61H 31/00* (2006.01)
*A61H 9/00* (2006.01)

(52) U.S. Cl.
CPC ............ *A61B 5/1135* (2013.01); *A61B 5/4815* (2013.01); *A61B 5/4836* (2013.01); *A61B 5/6805* (2013.01); *A61F 5/56* (2013.01); *A61H 9/0092* (2013.01); *A61H 31/00* (2013.01); *A61H 2201/0103* (2013.01); *A61H 2201/165* (2013.01); *A61H 2201/5007* (2013.01); *A61H 2201/5071* (2013.01); *A61H 2201/5087* (2013.01); *A61H 2205/08* (2013.01); *A61H 2230/405* (2013.01); *A61H 2230/505* (2013.01)

(56) References Cited

U.S. PATENT DOCUMENTS

| | | | |
|---|---|---|---|
| 5,453,081 | A | 9/1995 | Hansen |
| 5,769,084 | A | 6/1998 | Katz |
| 6,030,353 | A * | 2/2000 | Van Brunt ..................... 601/150 |
| 7,516,743 | B2 | 4/2009 | Hoffman |
| 2004/0143194 | A1* | 7/2004 | Kihara ................. A61B 5/1135 |
| | | | 600/534 |

OTHER PUBLICATIONS

Japanese Office Action for Japanese Patent Application No. 2013-513505, with a date of notice of Apr. 21, 2015 and English translation.

* cited by examiner

SYSTEM OVERVIEW

Front Panel

Side Panel

METHOD AND DEVICE(S) FOR DIAGNOSIS AND/OR TREATMENT OF SLEEP APNEA AND RELATED DISORDERS

REFERENCE TO RELATED APPLICATIONS

This application is a U.S. National Phase filing under 35 USC 371 of PCT/CA2011/000669 filed Jun. 8, 2011 claiming priority under 35 USC 119(e) from U.S. Provisional Patent Application No. 61/352,931 filed Jun. 9, 2010.

FIELD OF INVENTION

The present invention concerns a common approach to the diagnosis and treatment of sleep apnea and related disorders, such as Snoring and Respiratory Effort Related Arousals, that consists of applying positive pressure to the external surface of the chest and/or abdomen during part or all of the respiratory cycle, by use of an inflatable vest or cuff, in order to: a) make intra-thoracic pressure less negative during inspiration and/or b) make intra-thoracic pressure more positive during expiration and/or c) to slightly increase Vest pressure on a continuous basis. In applications a) and b) the system is intended to treat the Sleep-related disorders. In application c), the system is intended to simply monitor breathing in order to help diagnose these disorders. The diagnostic and therapeutic modes can be embodied in single or independent devices depending on intended use.

BACKGROUND TO THE INVENTION

Sleep Respiratory Disorders are disorders in which the flow rate into the lungs decreases during sleep to levels that are less than what is required to maintain normal blood gas tensions ($PCO_2$ and $PO_2$). Respiratory efforts increase in response, resulting in arousal from sleep or snoring depending on the severity and mechanism of the disorder and response characteristics of the respiratory control mechanisms. Sleep respiratory disorders manifest in different forms; Sleep Apnea, Snoring, and Respiratory Effort-Related Arousals (RERAs). Often the different forms are present in the same patient. The current invention should be beneficial in all these forms.

DIAGNOSIS OF SLEEP-RELATED RESPIRATORY DISORDERS: This is typically done overnight in a sleep laboratory or in the home by attaching a number of sensors to the body. A type of sensor that is essential for diagnosing such respiratory disorders is one that can sense the rate of air moving in and out of the patient. It is the pattern of change in such a signal that makes it possible to identify the presence of different types of disturbances. At present, there are three types of sensors that are used for this purpose. Because none of these is free of serious technical problems, it is customary to use all three in the same study. These sensors are: a) Nasal cannula pressure. Here, an open-ended tube is inserted in the nares. Changes in pressure at the tip of the tube are used to derive a semi-quantitative measure of flow. Although, when conditions are favorable, the signal provides a reasonably good indication of "relative" flow, conditions are frequently unfavorable such as when the nares is blocked or when the patient is breathing through the mouth. Also, the signal often becomes zero (i.e. signaling no flow), when some flow is still present, making it difficult to distinguish between apneas and hypopneas. b) Thermister: Here, a temperature sensitive sensor is placed in front of the nose and/or mouth. Changes in temperature are used to infer the direction and magnitude of flow. This signal cannot be quantified and is prone to serious drifts and artifacts, limiting its use to simply distinguish between, flow and no flow. c) Chest and abdomen bands: These are typically applied to the rib cage and abdomen. Changes in the impedance or inductance of these bands are used to infer changes in lung volume. Because changes in rib cage and abdomen dimensions are often not in phase with each other, it is necessary to perform complex calibrations to obtain the net change in lung volume. These calibrations also change frequently from time to time, making it impractical to use these signals for quantitative evaluation of breathing. As a result, the use of these bands is currently limited to determining if there are respiratory efforts and whether the rib cage and abdomen move in phase.

The current invention represents a totally new approach to monitoring breathing. Here, the subject wears an inflatable vest, cuff or garment with a pliable inner lining and a stiff outer lining. The vest is slightly pressurized (only 2-3 $cmH_2O$) on a continuous basis to cause the inner lining to mould around the subject's torso without causing any significant reduction in lung volume. Under these conditions expansion of the lungs will result in air moving out of the vest, and vice versa. The flow in and out of the vest (Vest Flow) can be measured. This signal reflects air moving in and out of the lungs regardless of whether such air movement results in expansion of the rib cage, the abdomen or both, whether the rib cage and abdomen move in-phase or out-of-phase and whether the patient is breathing through the nose or mouth. With some minor adjustments to the Vest Flow signal, the signal can even be made purely quantitative, a feature that is now only achievable by attaching accurate flow meters to face masks.

TREATMENT OF SLEEP-RELATED RESPIRATORY DISORDERS: Sleep apnea is a condition in which airflow into the lungs decreases markedly (hypopnea) or ceases completely (apnea) for brief periods. These periods of decreased or absent flow (collectively called apneas here) are followed by a ventilatory overshoot during which airflow is high with the result that the increase in carbon dioxide ($CO_2$) and decrease in oxygen ($O_2$) levels in the blood that occurred during the apnea is corrected or overcorrected. Because maintenance of adequate breathing requires certain levels of blood gas tensions, correction or over-correction of blood gas tensions during the overshoot sets the stage for recurrence of the apnea (Younes M. The Physiologic Basis of Central Apnea and Periodic Breathing. Current Pulmonology, 10:265-326, 1989. Younes M. Role of arousals in the pathogenesis of obstructive sleep apnea. Amer J Respir Crit Care Med. 169: 623-633, 2004; Younes M. Role of Control Mechanisms in the Pathogenesis of obstructive sleep disorders. J Appl Physiol 105: 1389-1405, 2008). Apneas can be obstructive or central.

The obstructive variety develops when the upper airway (pharynx) is narrow or excessively compliant and collapses under the influence of the negative pressure generated during the inspiratory phase. Normally, the upper airway of such individuals is kept open while awake by activity of pharyngeal muscles called the pharyngeal dilators (Dilators). The activity in these muscles decreases at sleep onset leaving the pharynx with little mechanical support. An apnea develops at sleep onset and continues until the subject awakens or until $PCO_2$ and $PO_2$ levels deteriorate sufficiently to activate the Dilators. When the Dilators are activated by arousal or by blood gas changes, the airway opens. Typically, in patients with obstructive apnea this is associated with a ventilatory overshoot (Overshoot) that overcorrects the blood gas changes, inhibiting the Dilators and resulting in another apnea.

One approach to preventing such recurrences, therefore, is to limit the changes in blood gas tensions that occur during the "open" phase of the cycle. Through such intervention blood gas tensions at the end of the ventilatory phase are not so corrected as to inhibit the Dilators.

The central Apnea variety is also characterized by recurrent cycles of decreased followed by increased flow but the mechanism of this instability is less dependent on upper airway mechanical abnormalities and more related to instability in the mechanisms that regulate blood gas tensions. As in the case of the obstructive variety, the instability may be mitigated by devices that limit the changes in blood gas tensions during the overshoot. Through such intervention blood gas tensions at the end of the overshoot are not so corrected as to inhibit the respiratory centers, thereby mitigating the occurrence of another apnea.

One approach that has been used to mitigate the changes of blood gas tensions during the overshoot is to increase the concentration of $CO_2$ in the inspired gas, through re-breathing or injection of $CO_2$ in the inspired gas. This kind of intervention requires that the patient be connected to the device that alters inspired gas via a facial interface. This is not well tolerated. Furthermore, in my experience the inhalation of $CO_2$ approach is difficult to control and often results in sleep disruption.

A totally new approach to mitigating the changes of blood gas tensions during the overshoot is to mechanically limit the overshoot itself by devices that oppose lung expansion during inspiration. This approach can be implemented by reducing airway pressure at the external airway during inspiration (negative pressure loading) or by application of positive pressure to the external chest wall (thorax and/or abdomen) during inspiration (positive pressure loading).

Negative pressure loading is impractical since it not only requires the poorly tolerated facial interface but the increased negative pressure in the airway will promote more upper airway collapse, which would be counterproductive.

External Positive Pressure Loading, however, can be applied with an inflatable vest or cuff applied to the ribcage and/or abdomen. Such a device would be better tolerated than other approaches that aim to reduce the over-ventilation that occurs at resumption of breathing (e.g. $CO_2$ breathing), or other approaches that are currently used to treat sleep apnea (e.g. Continuous Positive Airway Pressure (CPAP)). In addition, it has the considerable advantage of concomitantly reducing the negativity of intra-thoracic pressure during inspiration, which should mitigate the tendency for the upper airway to collapse during inspiration in susceptible individuals. This latter feature (making intra-thoracic pressure less negative during inspiration) also renders this approach (External Positive Pressure Loading) effective in less severe (than apneas) forms of upper airway dysfunction such as snoring and Respiratory Effort Related Arousals (RERAs).

Snoring: Snoring results from vibration of upper airway wall during breathing. It occurs in subjects with a collapsible airway in whom the abnormality is not severe enough to result in hypopnea or apneas either because the structure of the upper airway is not as abnormal or because the Dilators are more effective in preventing more serious collapse. Snoring is usually most prominent in the inspiratory phase although in some cases respiratory noises can be heard during expiration. In recent years I have been carrying out extensive studies using an approach I labeled Dial-down. In this approach patients with snoring (with or without apneas) are placed on CPAP to normalize their upper airway. On CPAP, upper airway resistance and blood gas tensions are normal and, as a consequence, their respiratory effort (negative intra-thoracic pressure) is not high. Intermittently, we reduce the CPAP level to induce a hypopnea or apnea. With such interventions (Dial-downs) the respiratory drive and effort remain low for a few breaths until the deteriorating blood gas tensions result in an increase in inspiratory effort and more negative intra-thoracic pressure. In my experience with thousands of such Dial-downs in >100 patients, snoring never occurs in the first few breaths after the Dial-down, and only develops sometime later. One possible explanation is that snoring requires high energy to vibrate the soft tissues of the airway and this level of energy develops only when respiratory efforts increase in response to deteriorating blood gas tensions. In such case by use of positive pressure loading during inspiration (as per our proposed invention), intra-thoracic pressure is rendered less negative, which should result in less snoring. It may be argued that the less negative intrathoracic pressure during inspiration will result in less flow and under-ventilation. However, in virtually all cases, snoring is associated with flow limitation at the upper airway. The hallmark of this flow limitation is that flow is independent of downstream pressure (intra-thoracic pressure in this case) or actually decreases as effort increases (Negative Effort Dependence). Thus, by reducing intra-thoracic pressure during inspiration inspiratory flow is not expected to decrease and may actually increase in the presence of Negative Effort Dependence, an added bonus.

Respiratory Effort Related Arousals (RERAs): This is an intermediate phenomenon between snoring and frank obstructive apnea. Here, flow limitation occurs at the upper airway but the level of flow is not sufficient to maintain a steady state. As a result, blood gas tensions slowly but progressively deteriorate resulting in a progressively increasing inspiratory effort and ultimately arousal (arousal occurs when a threshold level of effort (intra-thoracic pressure) is reached). Often flow rate decreases as effort increases in the course of the event. If the progressive decrease in flow rate during the event is related to negative effort dependence, application of external positive pressure during inspiration, by use of the current invention, should mitigate the effort-related decrease in flow. This could delay the arousal, making it possible in some patients to reach a steady state.

Progressive reduction in flow rate: As indicated above, flow rate often decreases breath-by-breath in the course of hypopneas, snoring or RERAs (Younes M. Contributions of upper airway mechanics and control mechanisms to severity of obstructive apnea. Amer J Respir Crit Care Med. 168:645-658, 2003; Schwartz A R et al. The hypotonic upper airway in obstructive sleep apnea: role of structures and neuromuscular activity. Am J Respir Crit Care Med 157: 1051-1056, 1998). Also as indicated above, this progressive reduction in inspiratory flow may be related to the progressive increase in inspiratory effort (Negative Effort Dependence). However, certain observations make it likely that other factors contribute to this progressive reduction in inspiratory flow rate. The most important of these observations is that the largest breath-by-breath reduction in inspiratory flow occurs between the first and second breaths of the hypopnea, where the difference in effort is negligible (Younes M. Contributions of upper airway mechanics and control mechanisms to severity of obstructive apnea. Amer J Respir Crit Care Med. 168:645-658, 2003). This temporal pattern indicates that the breath-by-breath reduction is, at least in part, related to progressive narrowing of airway dimensions even during expiration (i.e. is independent of instantaneous inspiratory effort). There are several mechanisms that could account for this progressive narrowing during expiration: First, as suggested by Schwartz et al (Am J Respir Crit Care Med 157: 1051-1056, 1998), progressive narrowing is related to progressive reduction in lung volume in the course of the event. Second, as suggested by John Remmers (personal communication), it may be the result of pharyngeal tissues being sucked in during successive inspiratory efforts while failing to completely recoil back during the expiratory phase. Third, as suggested by us (Younes M. Contributions of upper airway mechanics and control mechanisms to severity of obstructive apnea. Amer J Respir Crit Care Med. 168:645-658, 2003), progressive narrowing may be related to stress recovery following the phase of open airway. Thus, when the upper airway is widened during the ventilatory phase (or on CPAP) stress relaxation occurs, causing airway dimensions to progressively increase as a function of time. When the dilating force is removed at the onset of hypopnea, stress recovery occurs causing airway dimensions to decrease progressively as a function of time. The second and third mechanisms are both manifestations of visco-elastic behavior of the upper airway (hysteresis in the pressure-area relation) with the only difference between the two being that Remmers' explanation requires successive inspiratory efforts for narrowing to occur whereas with our explanation progressive narrowing would occur even without preceding inspiratory efforts. It is possible/likely that both the second and third mechanisms contribute. We strongly favor visco-elastic behavior (second and/or third mechanisms) over reduction of lung volume (first mechanism) as the cause of progressive narrowing of the airway in the course of obstructive hypopneas and RERAs (Younes M. Contributions of upper airway mechanics and control mechanisms to severity of obstructive apnea. Amer J Respir Crit Care Med. 168:645-658, 2003). Such progressive narrowing in the expiratory phase due to visco-elastic behavior can be reversed by applying positive pressure pulses to the chest/abdomen during expiration using the device of the present invention. These expiratory pulses would force the airway open during expiration, thereby making it easier for the dilators to keep the airway open during inspiration.

It is evident from the above discussion that positive pressure applied externally during the inspiratory phase may be beneficial with certain Sleep Respiratory abnormalities, whereas positive pressure applied externally during the exhalation phase may be beneficial with other abnormalities. It is also clear that these different types of abnormalities may coexist in the same patient. Thus, application of the positive pressure in both phases may also be beneficial. This can take the form of two independent pulses, one during inspiration and one during expiration. Alternatively, the positive pressure may be applied throughout the respiratory cycle. The latter continuous type of pressure application has the potential disadvantage of causing a reduction in lung volume, which is believed to result in narrowing of the upper airway because of reduction in axial traction on the upper airway (as a result of a higher diaphragm position). This complication can be mitigated by applying the continuous pressure only during obstructive events where it cannot reduce lung volume, or by compressing the rib cage only. While compression of the rib cage alone is less effective in increasing intra-thoracic pressure than compression of the rib cage and abdomen together, it has the advantage of forcing the diaphragm downwards, thereby increasing axial traction on the upper airway.

SUMMARY OF THE INVENTION

The basic approach herein is to apply an inflatable vest, cuff or other inflatable or pressurizable implement, hereby collectively called VEST, to the external surface of the torso, continuously maintaining a low pressure level in said Vest (holding pressure) to effect close contact between the inner layer of the Vest and the Torso, monitoring flow in and out of the vest and, optionally, pressurizing said VEST at specified times during the respiratory cycle such that expansion is opposed when the positive pressure is applied during inspiration whereas exhalation is promoted when the pressure is applied during the exhalation phase. Continuous pressure application above the holding pressure during obstructive events may also be used.

Because the external pressure may need to be applied during specific phases of the respiratory cycle, such devices should preferably be equipped with means to identify the respiratory phases of breathing and preferably to provide a quantitative measure of changes in torso volume and the rate at which torso volume increases (i.e. patient flow rate). This can be achieved by placing sensors on the torso or in the material surrounding the torso that detect external torso dimensions, by suitable calibration of the flow of gas in and out of the VEST (see preferred embodiment), or by other means such as estimating flow rate by nasal cannula or by a flow meter attached to a facial interface (face or nose mask).

The pattern of increase in pressure during the inspiratory or expiratory phase will vary depending on the application:

1) For snoring and RERAs, if the mechanism is excessive negative inspiratory pressure, the applied external pressure may take the form of a ramp that begins after an adjustable delay from the onset of inspiration and progresses to a maximum adjustable level, remaining at that level for an adjustable duration or until the end of the inspiratory phase. Alternatively, if the snoring and progressive reduction in flow are not related to the magnitude of inspiratory negative pressure but are due to a critically narrowed airway, positive pulse may be applied during the exhalation phase to transiently widen the airway, thereby causing some stress relaxation (dilatation) that lasts for several breaths. Determination of which pattern is needed can be established in a calibration study in the sleep laboratory or in the home by an attendant who tries the different patterns while the subject is asleep. In either case, the delay, adjustable maximum level, the rate of increase in pressure, the duration of the applied pressure and/or the frequency of applying the pulses may be preset based on knowledge of what pattern is needed to eliminate snoring in the particular patient (during a titration procedure) or may be automatically adjusted by circuitry that detects snoring sounds or magnitude of flow limitation and dynamically adjusts these variables to eliminate correct the problem. Other patterns may be used that accomplish the objective of reducing or eliminating snoring.

2) For treatment of sleep apnea (obstructive or central) the primary objective is to reduce the overshoot at the end of the apneas. Thus, the external pressure is preferably made proportional to inhaled volume or flow rate, thereby causing the opposing force to increase during the overshoot and to decrease during the hypopnea/apnea phase. In patients in whom progressive reduction in flow rate is present during the hypopnea phase, a preset ramp increase in external force during inspiration and/or exhalation may be applied during the hypopnea phase to be replaced by volume- or flow-related increase in force during the overshoot phase.

Accordingly, in one aspect of the present invention, there is provided a method for diagnosing and/or treating sleep apnea and related disorders, such as snoring and respiratory effort-related arousals, comprising:

applying an inflatable implement to the external surface of the chest and/or abdomen of a patient (Vest), said implement being capable of exerting positive pressure to said chest and/or abdomen of said patient, causing pressure within said Vest to rise continuously to a set positive value (Continuous Pressure), and monitoring the rate of airflow into and/or out of said Vest (Vest Flow), whereby said Vest Flow is displayed or processed to obtain information about the breathing characteristics of said patient.

In another aspect of the present invention, there is provided a device for diagnosing and/or treating sleep apnea and related disorders, such as snoring and respiratory effort-related arousals, comprising:

an inflatable implement that can be applied to the external surface of the chest and/or abdomen of a patient (Vest), said implement being capable of exerting positive pressure to said chest and/or abdomen of said patient, a positive pressure source, tubing connecting said positive pressure source to said Vest, electrical and/or digital circuitry that controls said pressure source and is capable of causing pressure within said Vest to rise continuously to a set positive value (Continuous Pressure), and circuitry to monitor the rate of airflow into and/or out of said Vest (Vest Flow), whereby said Vest Flow is displayed or processed to obtain information about the breathing characteristics of said patient.

DESCRIPTION OF THE PREFERRED EMBODIMENT

Figure 1:
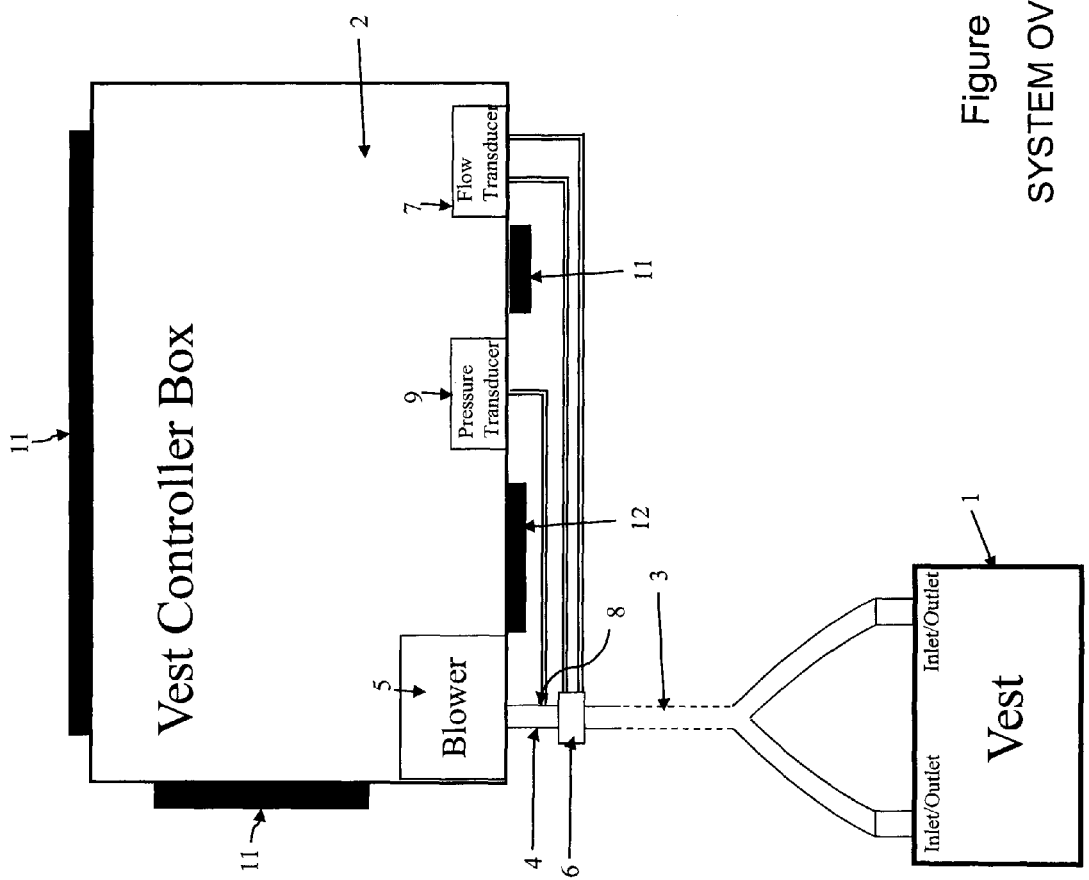
FIG. 1 is a system overview of a preferred embodiment of the present invention.
Figure 7:
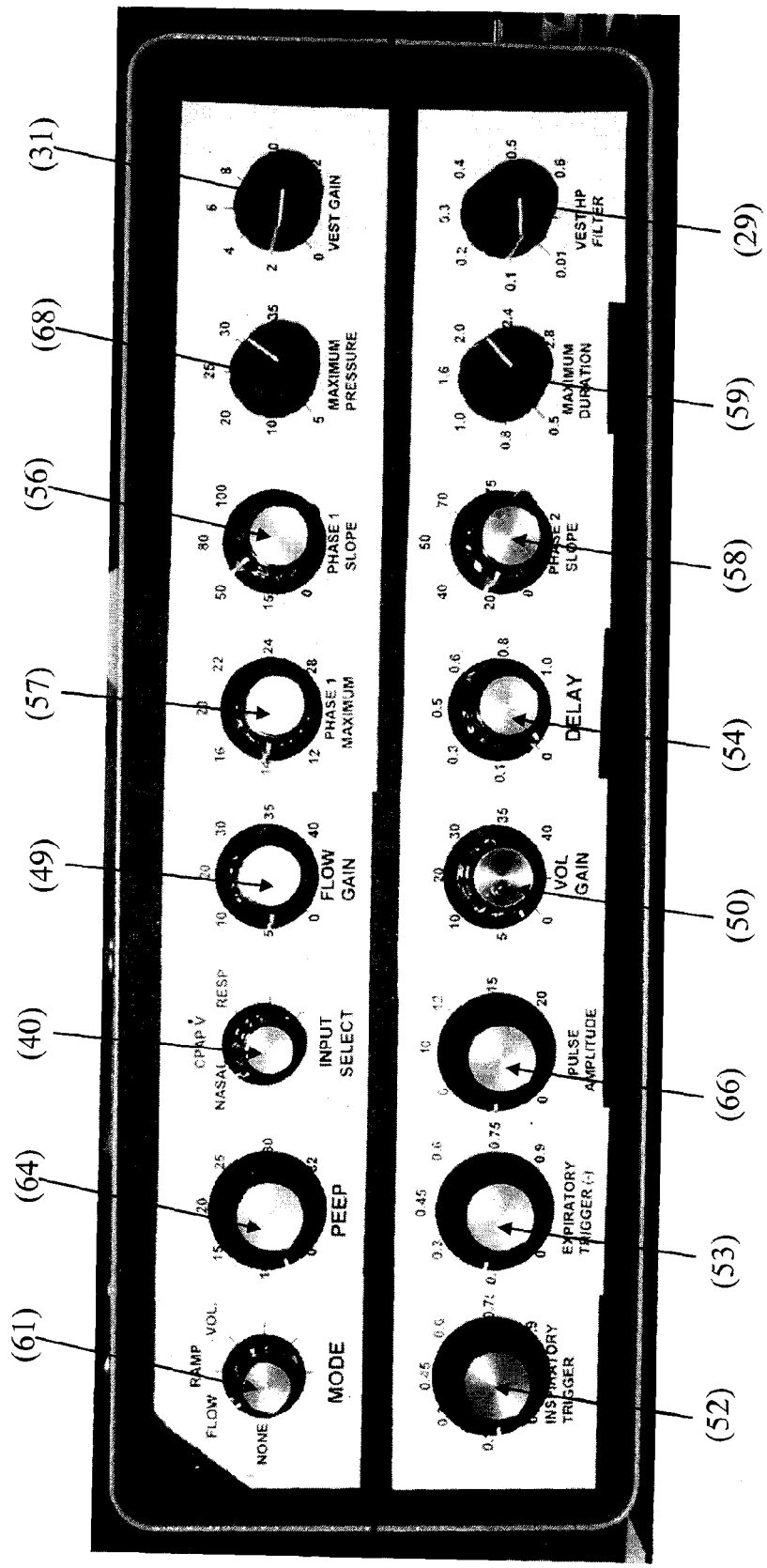
FIG. 7 is a front elevational view of the Controller box showing various external control knobs.
Figure 8:
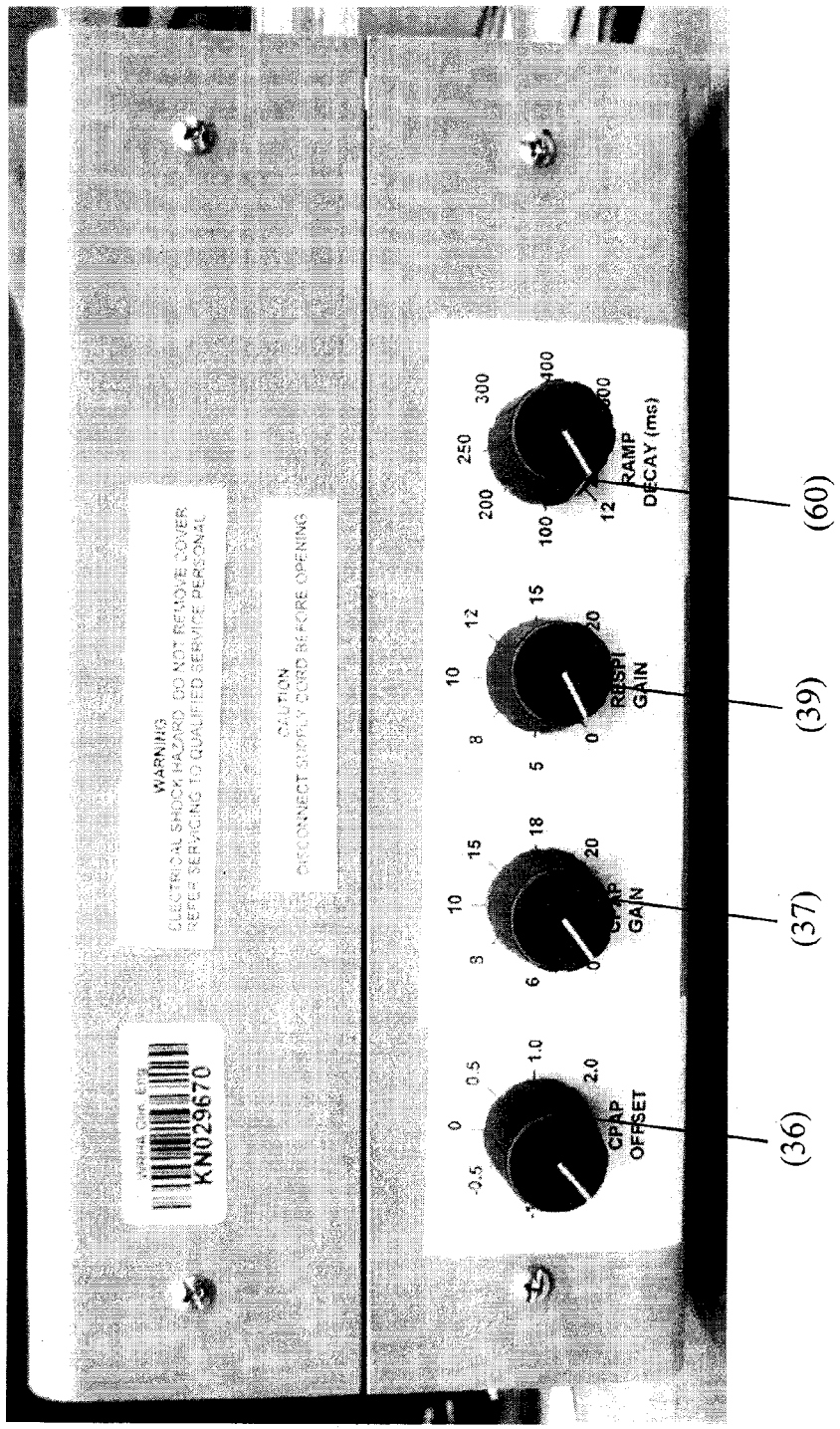
FIG. 8 is a side elevational view of the Controller box showing additional external control knobs.
Figure 9:
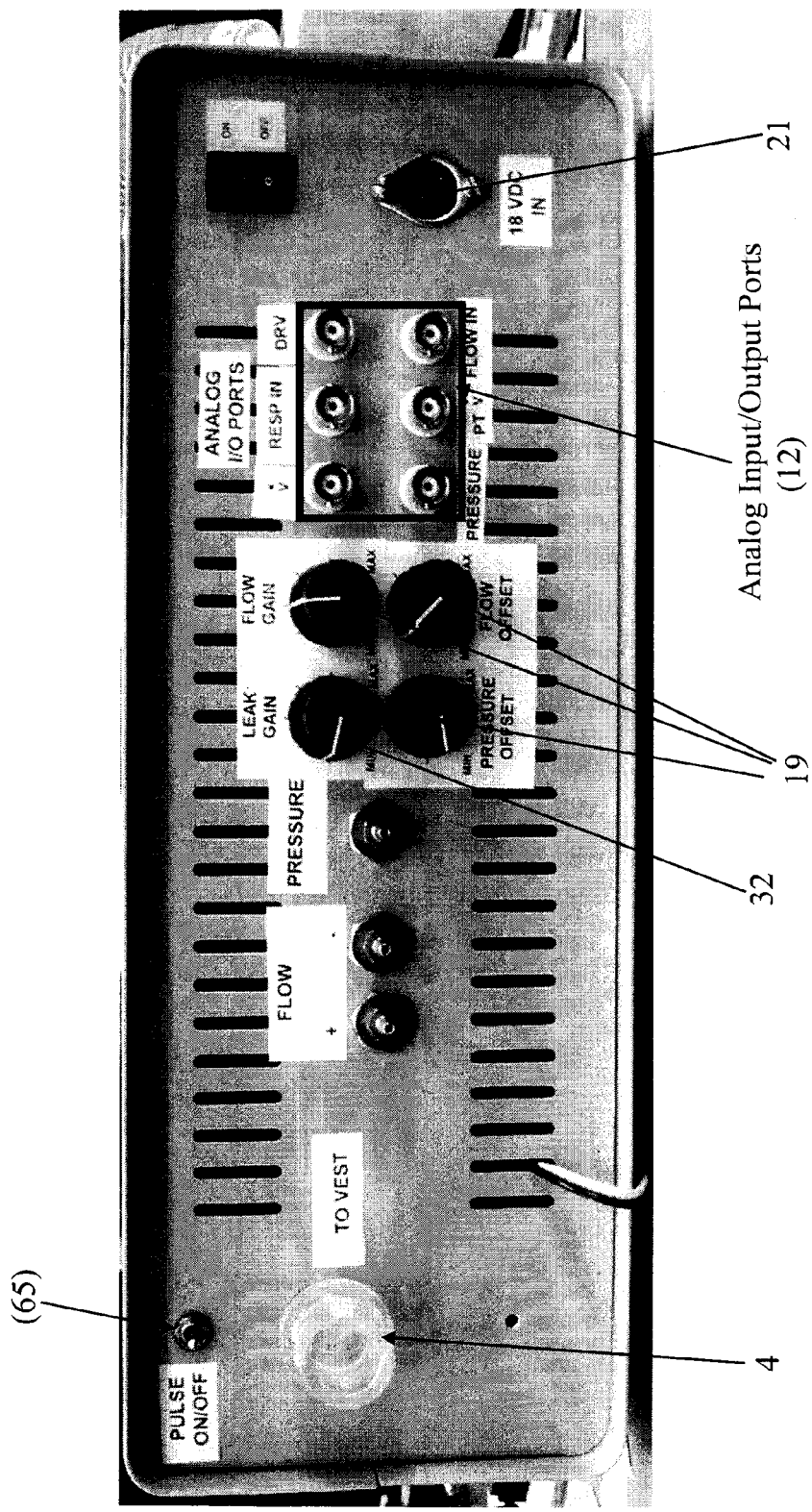
FIG. 9 is a back elevational view of the Controller box showing additional external control knobs and Input/Output analog ports.

Design:

An overview of the preferred embodiment is shown in FIG. 1. It is comprised of an inflatable vest, a controller box (2) and flexible tubing (3) to connect the inside lumen of the vest (1) to the output (4) of a blower (5) located inside the Controller Box (2). A suitable flow meter (6) is inserted in the tubing (3) close to the Box (2). While a flow meter of any type can be used, we use a Fleisch pneumotachogram and connect its two ports to the two ports of a differential pressure transducer (7) inside the box. A small port (8) in the tubing (3) is connected to a port of another pressure transducer (9) inside the Box (2) to measure tubing pressure. Although the flow meter (6), pressure port (8) and their connections are located outside the Box (2) in this embodiment, they can optionally be located inside the Box (2). A number of control knobs (11) are located on the front, side and back of the box (FIGS. 7 to 9). Additionally, analog input/output sockets (12) are available to introduce auxiliary input signals and to output desirable signals for display purposes or to control other devices.

Figure 2:
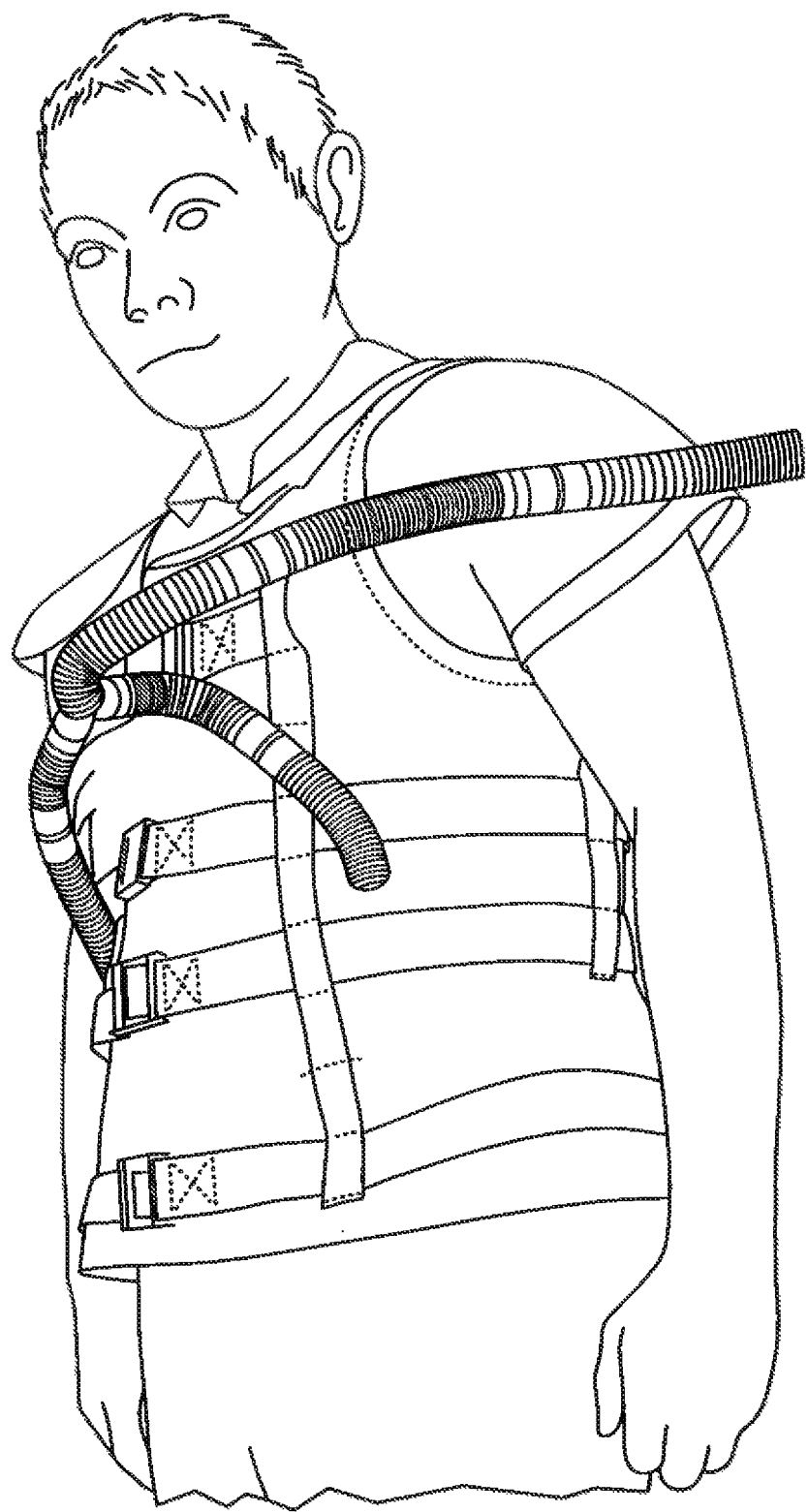
FIG. 2 illustrates the Vest applied to a subject with tubing attached.

The Vest (1) is a custom inflatable garment that envelops the torso from the shoulders to the upper rim of the hipbone (FIG. 2). The interior wall is made of highly pliable material (latex sheet, 0.4 mm thick) that can easily mold itself around the torso. The outer wall is, by contrast, made of stiff cloth that resists stretch. To minimize external expansion, a number of non-stretchable straps (13) are applied to the external surface of the vest (1). The vest is fabricated in different sizes to suit subjects of different stature. Clearly other vest models can be used. For continuous positive pressure application to the torso (as opposed to pressure pulses), a vest that envelops the rib cage only is preferred (see paragraph 0017).

Figure 3:
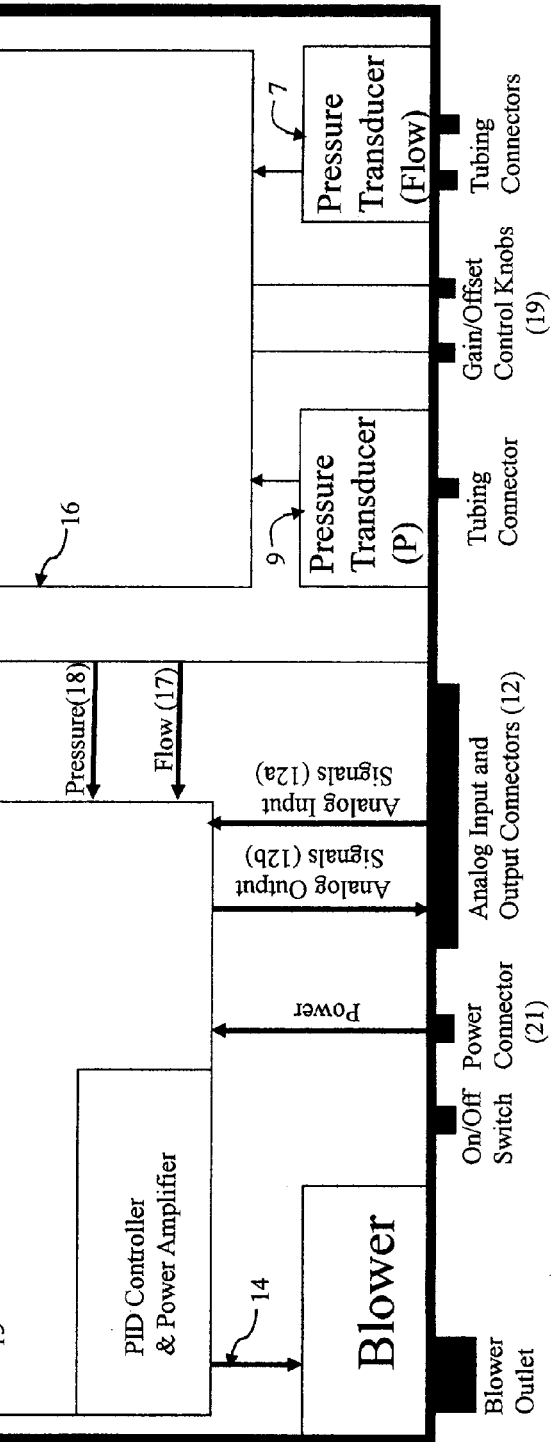
FIG. 3 is a block diagram of signal conditioning and control circuitry.
Figure 4:
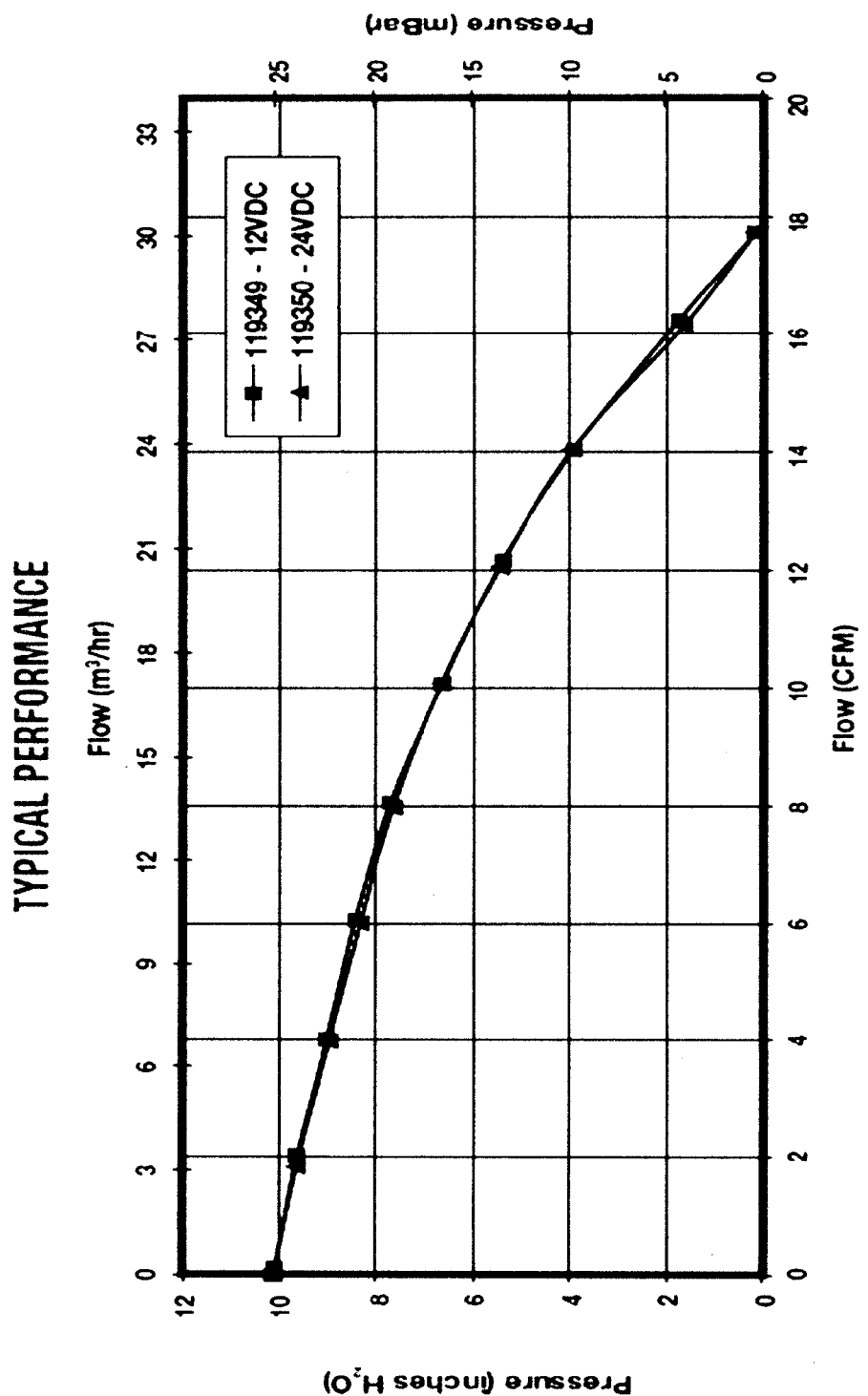
FIG. 4 is a graphical representation of a typical performance of the blower in the preferred embodiment of the invention shown in FIG. 1.

A diagram of the interior of the controller box (2) is shown in FIG. 3. A blower (for example, Ametek Microjammer 119349-01) (5) is located in the back of the Control Box (2) to pump air into the vest in order to increase the pressure within the vest. Because of the stiffness of the external vest wall and the highly compliant interior vest wall, vest pressure is transmitted almost completely to the body surface. The blower (5) used in this prototype is capable of generating a static pressure of 25 cmH2O, and a maximum flow, at zero pressure, of 8.0 L/second (FIG. 4) but, clearly, other models with different pressure and flow ranges can be used. Blower speed is controlled by a voltage output (14) from the Pressure Controller Board (15).

The Flow transducer (7) used is a Honeywell pressure transducer (DC005NDC4). The pressure transducer (9) is also a Honeywell transducer (Honeywell DC030NDC4). Other suitable transducer may be used. The outputs of both transducers are processed by standard electronic circuitry (16) that generates electrical signals that can be calibrated to provide an estimate of flow (17) and pressure (18) within the tubing. Calibration of the flow signal is typically 1V/L/s and for pressure is typically 1V/10 $cmH_2O$. External knobs (19) are located at the back of the Box to adjust offset and gain of the two signals. The Signal Conditioning Board (20) that contains the transducers (7, 9) and associated circuitry (16) is powered from the Pressure Controller Board (15).

Figure 5:
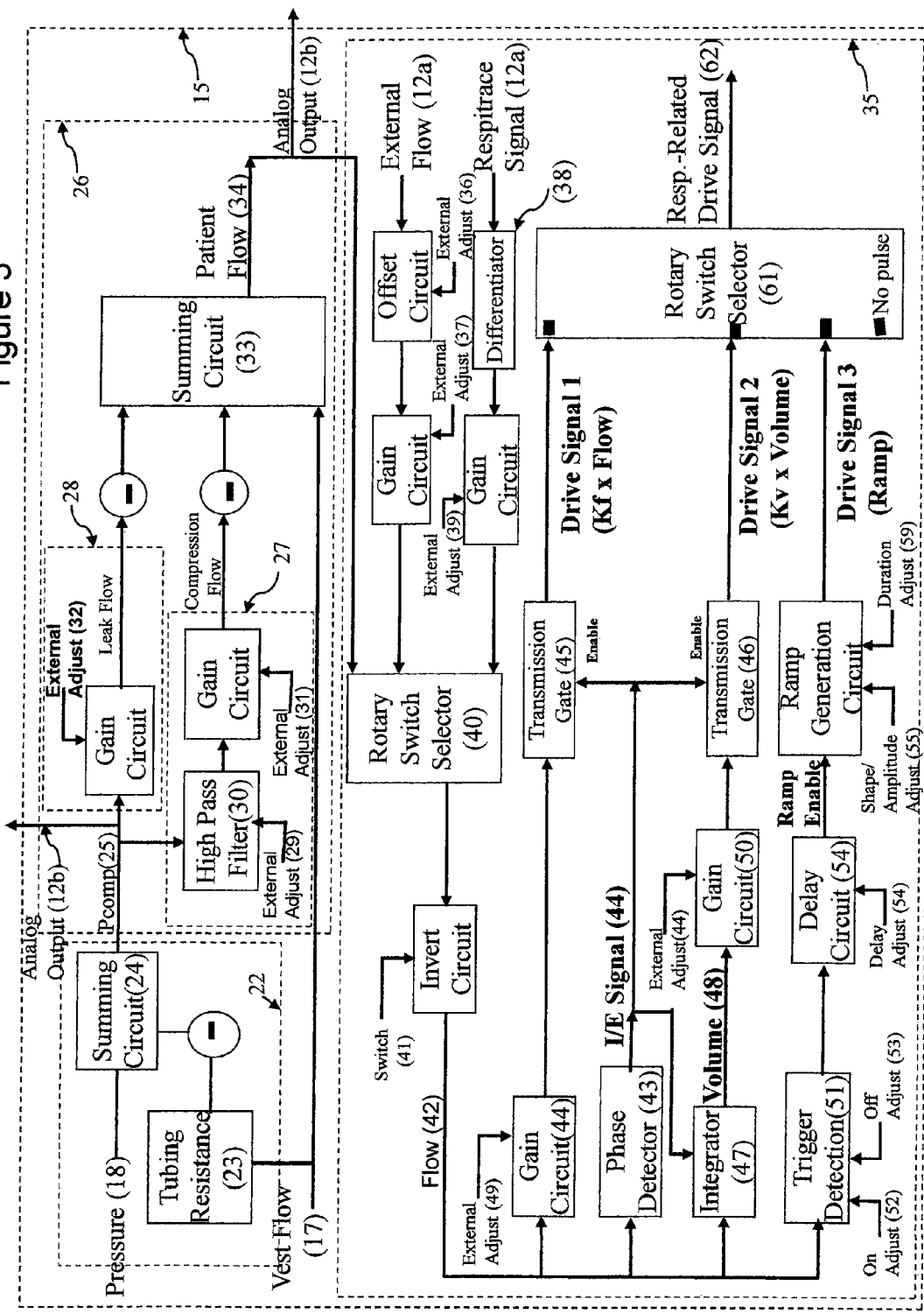
FIG. 5 shows details of circuitry that generates the drive signal for increasing Vest pressure according to specified functions linked to the respiratory phase of breathing.

The Pressure Controller Board (15) is powered by an 18 volt DC Adapter that is connected to the box through a power connector (21). The Board (15) contains circuitry that executes a variety of functions, as shown in FIG. 5 and described below:

Compensation for Tubing Resistance (22): To estimate the pressure in the Vest it is necessary to subtract the resistive pressure losses between the site of pressure measurement and the Vest. This is given by Vest Flow*Tubing resistance. A gain circuit (23) receives the Vest Flow signal (17). The gain is adjusted to match the known resistance of the tubing. The output of the gain circuit is subtracted from the pressure signal (18) using a summing circuit (24). The output of the summing circuit (Pcomp (25)) is optionally outputted via an analog output port (12b).

Circuitry to monitor the rate of lung expansion (Patient Flow): Patient Flow can be estimated using independent devices (e.g. nasal cannula, CPAP machines or processed respiratory band signals) and inputted directly into the Pressure Controller Board using an Analog Input Connector (12). Alternatively, Patient Flow can be estimated from Vest Flow (17) after compensating for leaks and gas compression effects. The flow rate through the tubing (Vest Flow (17)) incorporates two, and at times three, components. First, changes in vest pressure are associated with air movement in and out of the vest, independent of changes in the volume of the torso. Thus, at a constant torso (lung) volume, an increase in vest pressure is associated with air flowing into the vest (positive Vest Flow), and vice versa. The flow associated with changes in vest pressure (referred to as Compression Flow) is a function of the rate of increase in pressure (dP/dt), the compliance of the Vest (C), and the resistance of the tubing between the site of pressure measurement and the Vest (R). The product of the latter two factors (RC) is the time constant of the tubing/Vest system. Second, at a given vest pressure, changes in lung volume, as reflected in torso volume, result in air flowing in and out of the vest. When the torso expands air must flow out of the vest, and vice versa. The flow rate in and out of the vest resulting from lung expansion is inversely proportional to Patient Flow. Third, in the presence of leaks in the Vest, air flows into the Vest to maintain the pressure. The leak rate (Leak flow) is a function of Vest pressure (P). Thus:

Vest Flow=$fdP/dt+fP$−Patient Flow

Rearranging:

Patient Flow(inspiration negative)=Vest Flow−$f*dP/dt$−$fP$

The circuitry to estimate Patient Flow from Vest Flow (26) incorporates a circuit to estimate Compression Flow (27) and another circuit to estimate Leak Flow (28). The Compression Flow circuit (27) comprises an externally adjustable (for example, 0.0127 Hz. to 0.63 Hz). (29) high pass filter (30), in series with an externally adjustable gain circuit (0-12.4) (31). The high pass filter (30) receives the compensated pressure signal (25). The Leak Flow Circuitry (28) also receives the compensated pressure signal (25). This circuit (28) simply consists of an externally adjustable (32) gain factor to be applied to the pressure signal. We found that leaks out of this Vest system are nearly linearly related to pressure. The outputs of the two circuits (27, 28) are then subtracted from Vest Flow (17) using a Summing circuit (33), with the result being Patient Flow (34).

The circuits for delivering pressure pulses during selected parts of the respiratory cycle are shown in the bottom section of FIG. 5 (35). The Patient Flow Signal (34) generated from the Vest Flow signal (17) is only one possible input to control the timing of delivery of additional pressure pulses delivered during selected portions of the respiratory cycles. At times it is desirable to use other signals for such triggering. This is particularly the case when the airway is completely obstructed. In such cases a signal from one of the chest bands (e.g. Respitrace) may provide a better signal to identify respiratory phases. Also, under some circumstances where the signal derived from Vest Flow is of poor quality (due to imperfect compensation for Compression Flow during pulse application), other flow signals obtained independently (e.g. from a nasal cannula or a CPAP machine) may be used for triggering pulses. For these reasons, the preferred embodiment can accept one external analog flow input (12a) and a Respitrace input (12a). External knobs are available to adjust the offset (36) and gain (37) of the external flow input. The Respitrace signal is initially differentiated (38) to provide the rate of expansion (i.e. Flow). The signal is then amplified using an external gain control (39). An external Rotary Switch (35) allows selection of which of the three signals is to be used for pulse triggering. The selected flow signal can be used as is or after inversion (41). This determines whether pulses are delivered during the inspiratory or expiratory phase.

Determination of the respiratory phase in which Vest pressure increases. For this function, the selected flow signal (42) is passed through a Phase Detector with hysteresis (43). A TTL pulse (44) is generated when the flow signal exceeds a threshold amount (say, 0.04 L/sec) and the TTL pulse lasts until flow decreases below −0.04 L/sec. The polarity of the flow signal, as selected by the Inverter (41) determines whether the TTL pulse will be generated during inspiration or expiration. When the TTL pulse is on, transmission gates (45, 46) are open and an integrator (47) integrates the flow signal providing a signal that is proportional to inspired or expired volume (48).

In one type of pressure application the pressure rises in proportion to inspired or expired flow. With this type of pressure application what is adjusted is the proportionality between pressure and flow. This is accomplished by passing the flow signal through an externally adjustable gain circuit (49). The suitably amplified flow signal is then transmitted to a transmission gate (45) that is open only during the selected phase of breathing (44).

In another type of pressure application, the pressure rises in proportion to inspired or expired volume. With this type of pressure application what is adjusted is the proportionality between pressure and volume. To implement this function, the volume signal (48) is passed through an externally adjustable gain circuit (50) and then to a transmission gate (46) that is open only during the selected phase of breathing (44).

In yet another type of pressure application, the pressure rises according to a specified ramp function. Here the flow signal (42) is passed through a trigger detection circuit (51) with adjustable trigger sensitivity controls that determine the flow levels at which the ramp function will be initiated (52) and terminated (53). An adjustable delay circuit (54) determines how long after the On switch (52) the Ramp will be enabled. The shape and amplitude of the ramp are adjustable by several external knobs (55). Thus, the rising phase of the ramp is broken into two phases. The pressure pattern of phase 1 is specified by two knobs. Phase 1 slope adjust (56, FIG. 7) determines the rate of rise of pressure, and Phase 1 Max (57, FIG. 7) determines the highest level to be reached during phase 1. Phase 2 begins when maximum phase 1 pressure is reached. During phase 2 pressure rises at a rate determined by phase 2 slope knob (58). Phase 2 continues until a maximum duration is reached, as determined by a maximum duration adjust knob (59). The rate of decay of pressure at the end of the ramp is also externally adjustable (60).

Figure 6:
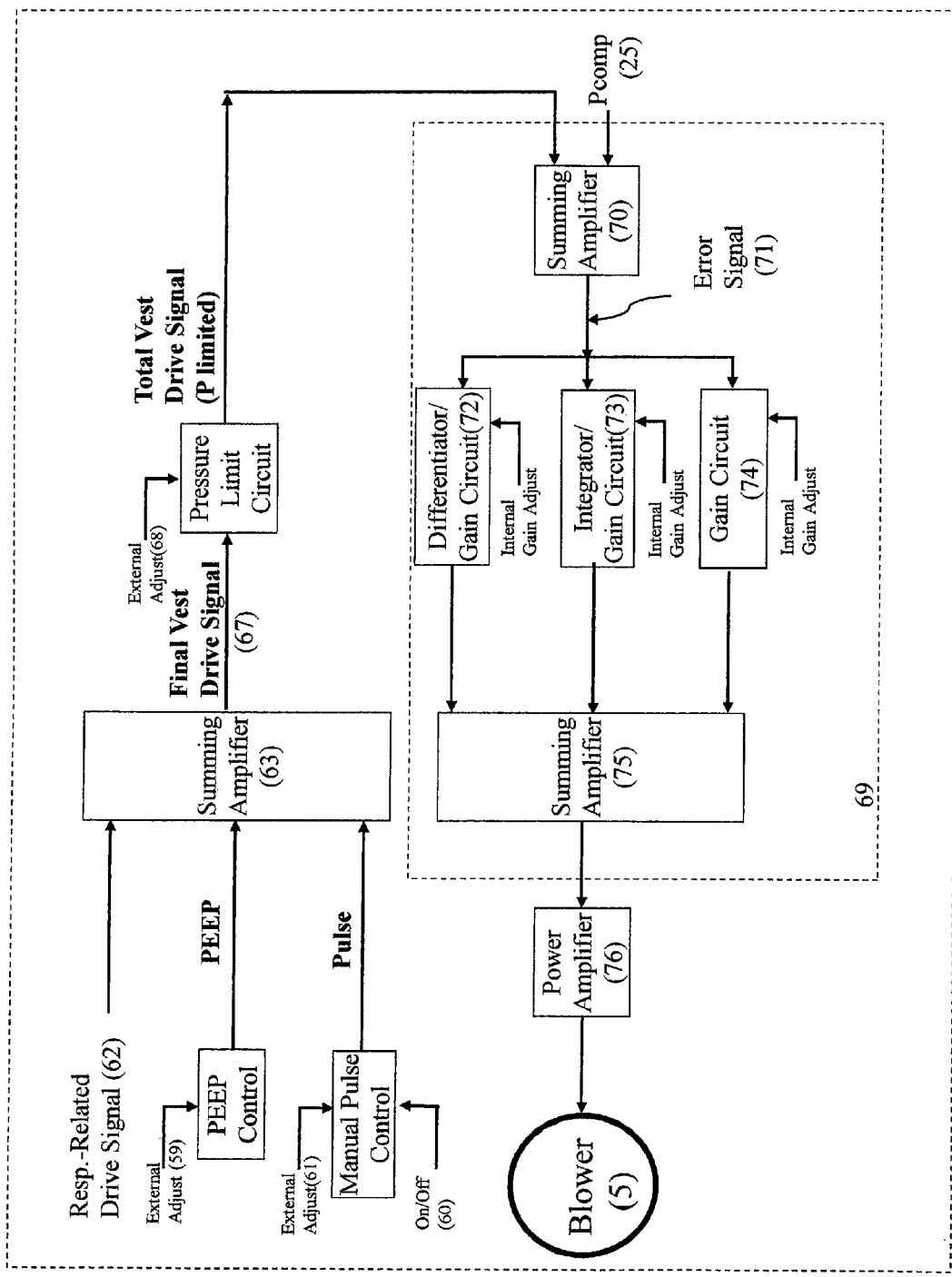
FIG. 6 shows the processing of the various drive signals and the PID controller for controlling blower speed.

The three possible drive inputs for respiratory phase-related pressure increases (flow-proportional, volume-proportional and ramp functions) converge on an external Rotary Switch Selector (61) that has four positions, one for each of the three pulse functions and one for "no pulse". This permits the selection of which function will be applied during the selected respiratory phase. The selected Respiratory-related Drive signal (62) is then passed to the Blower Drive Circuitry (FIG. 6). In the "no pulse" position the device simply delivers constant pressure (PEEP).

The final Drive Input to the blower circuitry is made up of three components, added together by a summing amplifier (63, FIG. 6). As indicated earlier, a small amount of constant pressure is required to prime the Vest and make its volume sensitive to changes in torso volume. This input (Positive End-Expiratory pressure, PEEP) is controlled by an external knob (64). The second input is the Respiratory-Related Drive Input (62) derived from the circuitry described in FIG. 5. The third input is a manual input that can be delivered at any time by use of an external toggle switch (65), located on the back of the controller box. This input is a square wave, with an externally adjustable amplitude (66) that lasts as long as the switch (65) is on. For safety reasons, the switch recoils to the neutral position when not manually activated. The Final Drive Input (67) is pressure limited by an externally adjusted knob (68).

The Final Drive Input (67) controls blower speed through a standard PID controller (69, FIG. 6), comprising a summing amplifier (70) that calculates the error signal (71) (i.e. difference between desired pressure (67) and actual compensated pressure (25)), a differentiator with an internally adjustable gain circuit (72), an integrator with an internally adjustable gain circuit (73) and an internally adjustable gain circuit applied to the error signal itself (74) to provide the proportional component of the feedback. The derivative (72), the integral (73) and proportional (74) components are summed by a summing amplifier (75). The output of the summing amplifier (75) is then suitably amplified with a power amplifier (76) which controls the speed of the blower (5).

Figure 10:
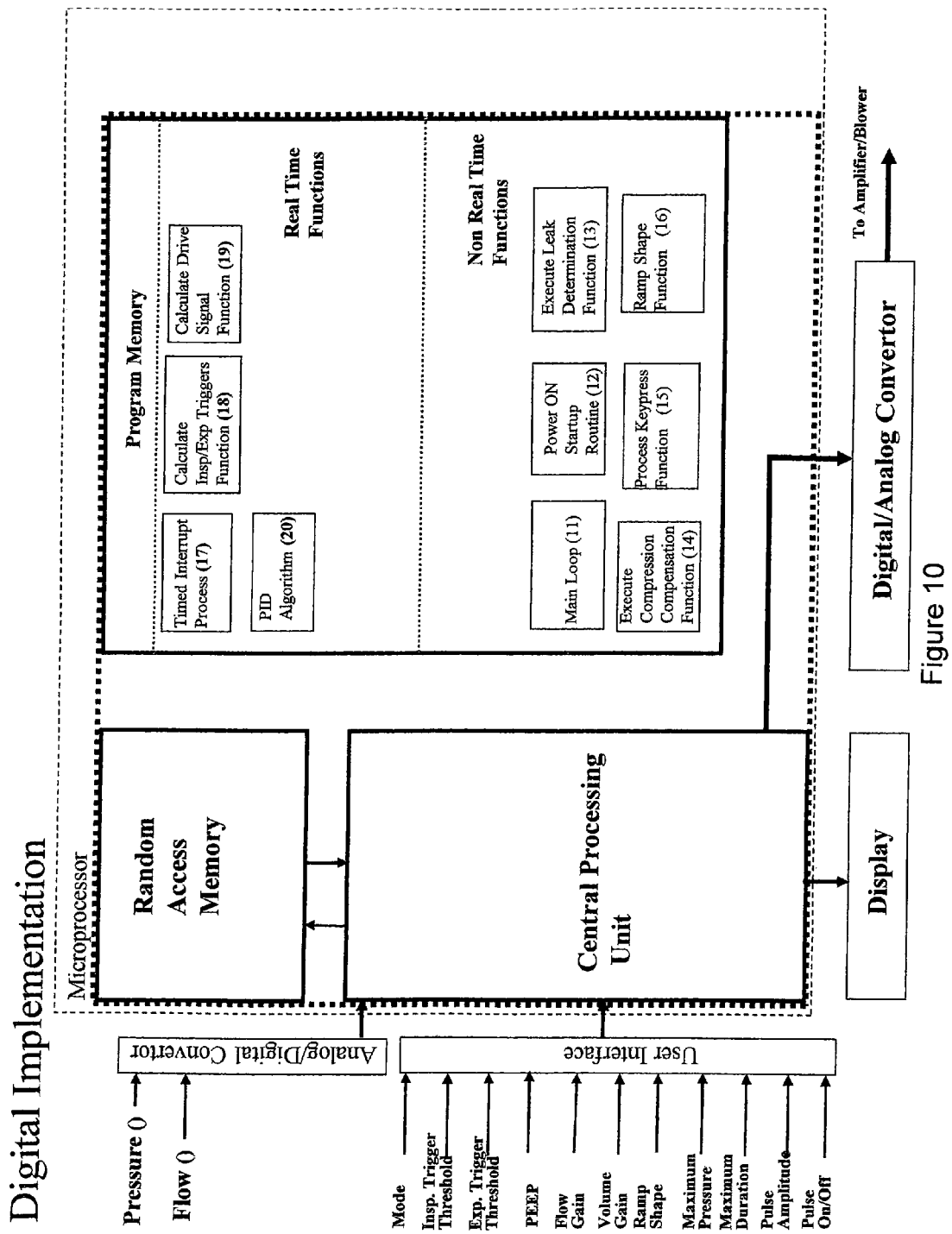
FIG. 10 is a block diagram of a digital implementation of the present invention. Numbers within different functions in the right block denote the Figure number containing the flow chart for the specified function.
Figure 11:
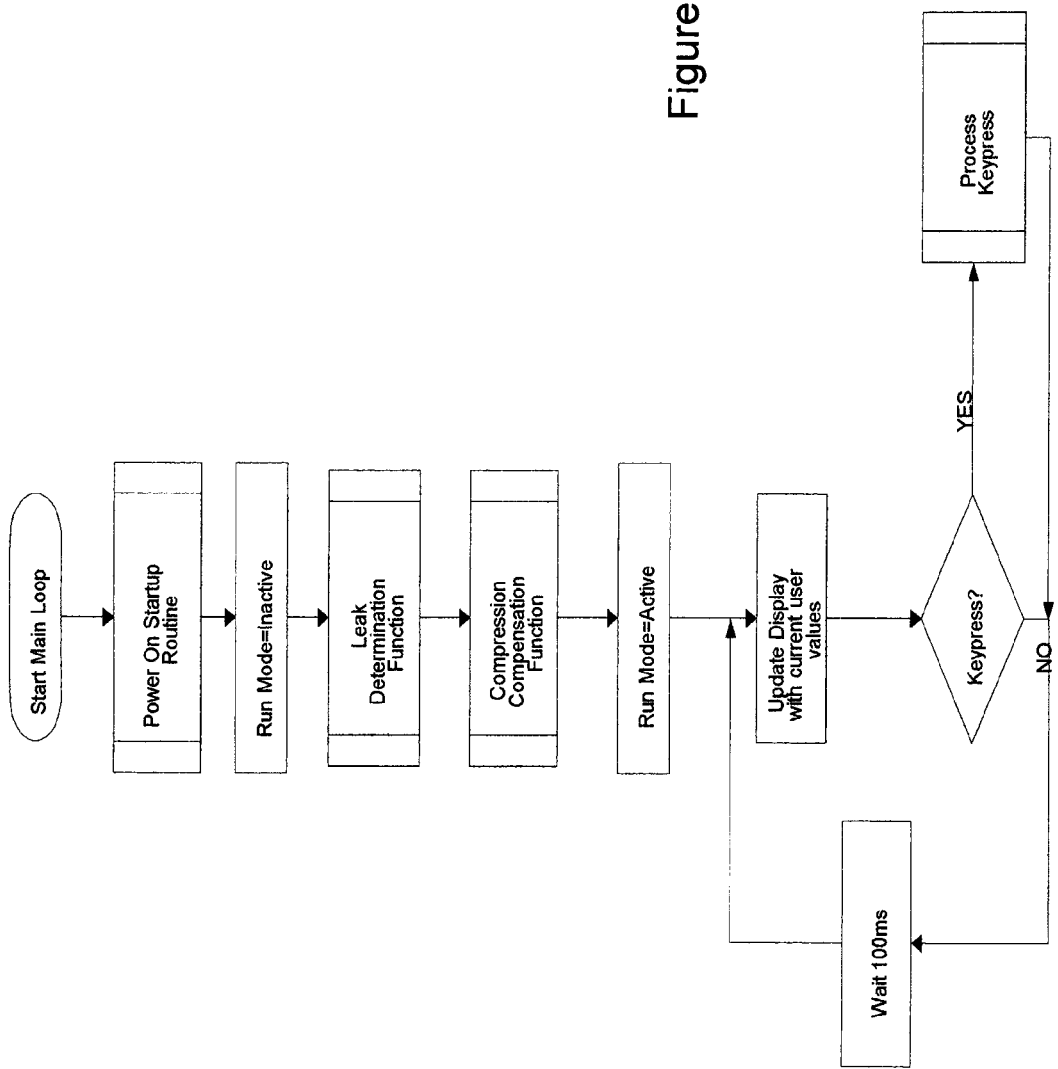
FIGS. 11 to 20 are flow charts describing the implementation of the different functions specified in FIG. 10.
Figure 12:
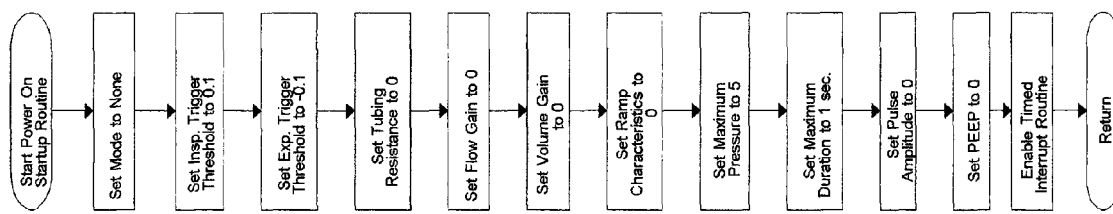
Figure 13:
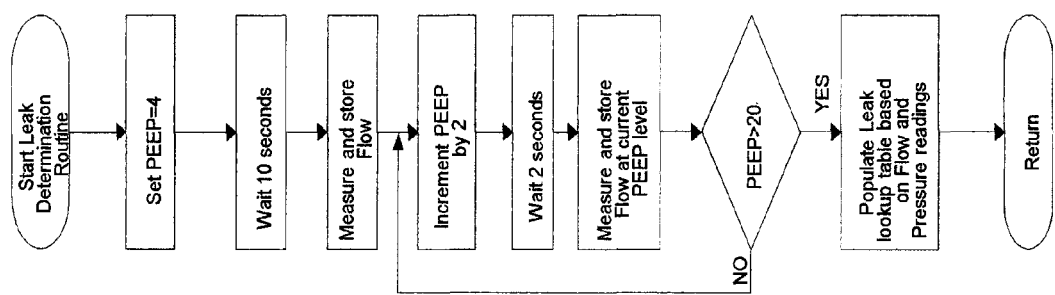
Figure 14:
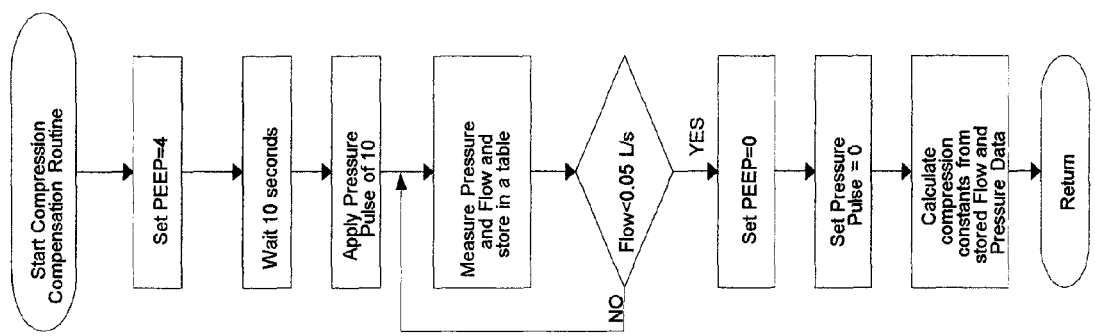
Figure 15:
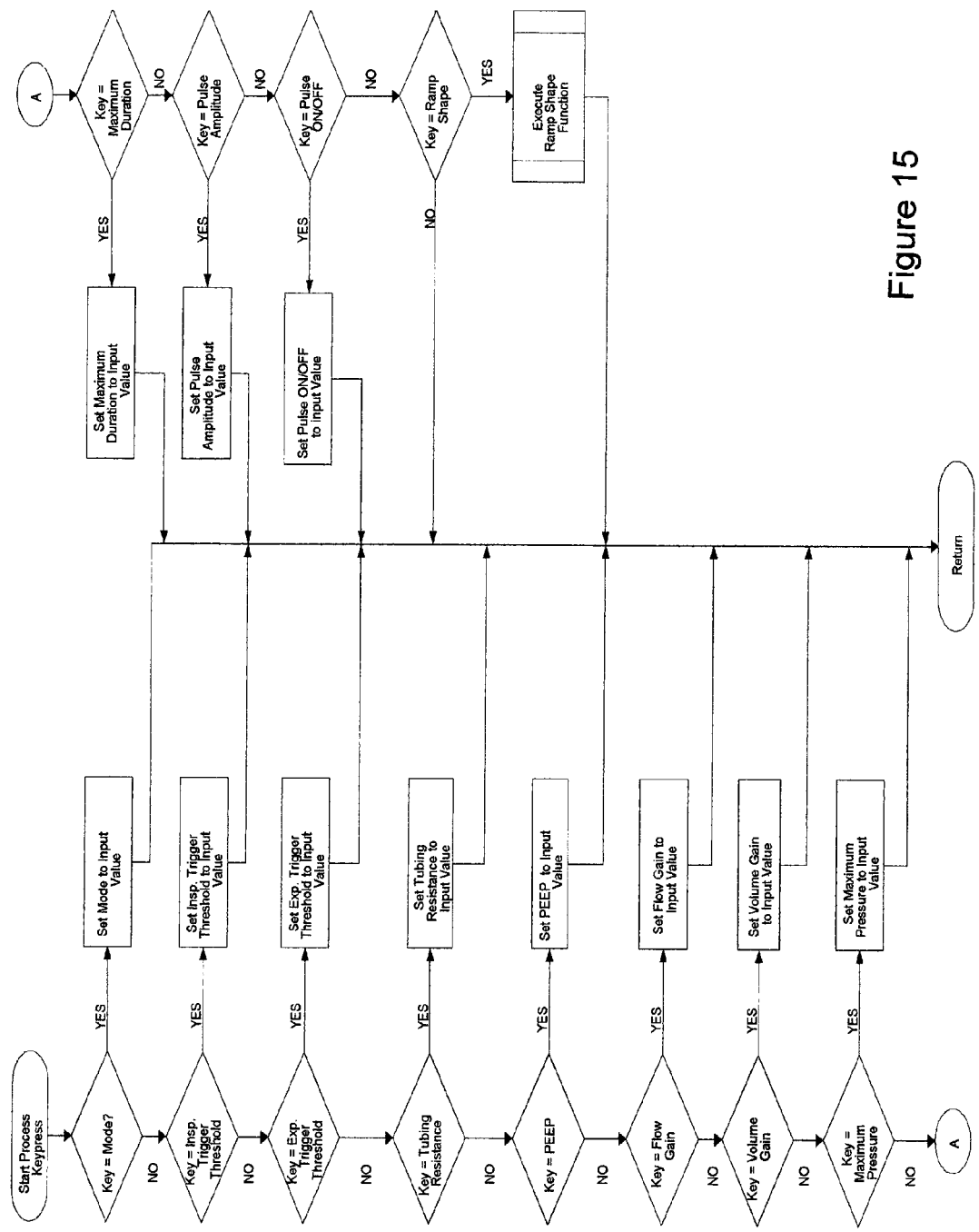
Figure 16:
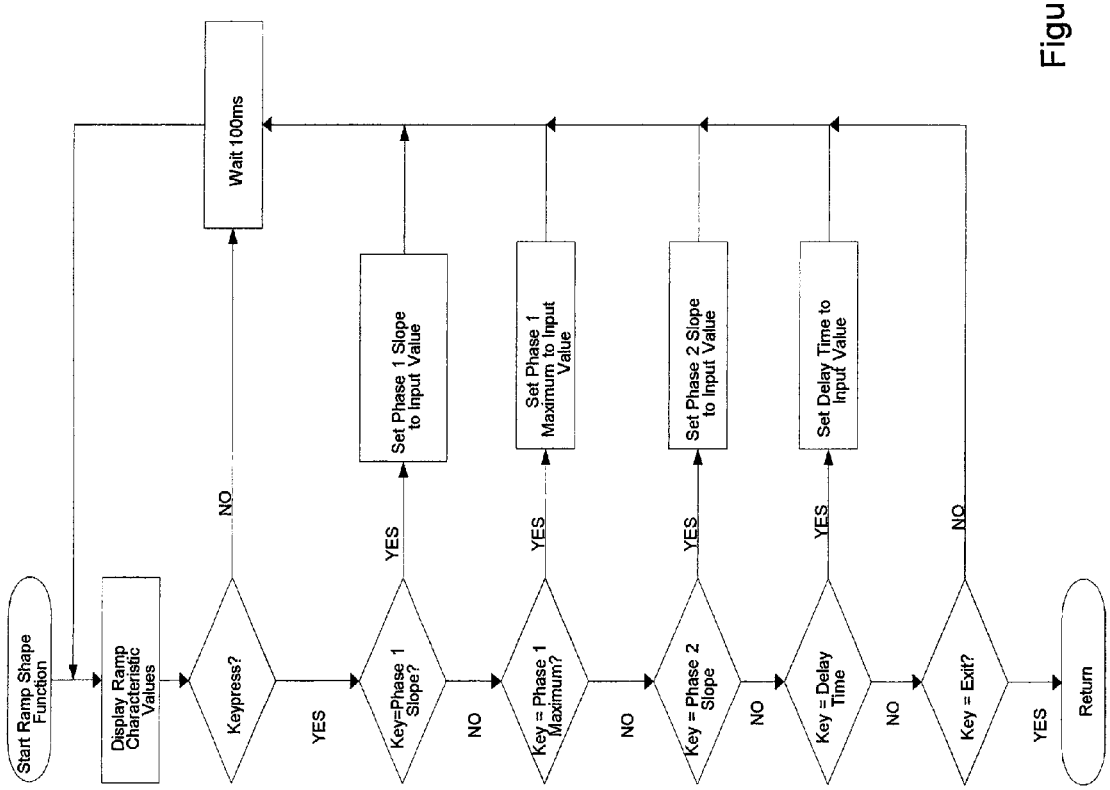
Figure 17:
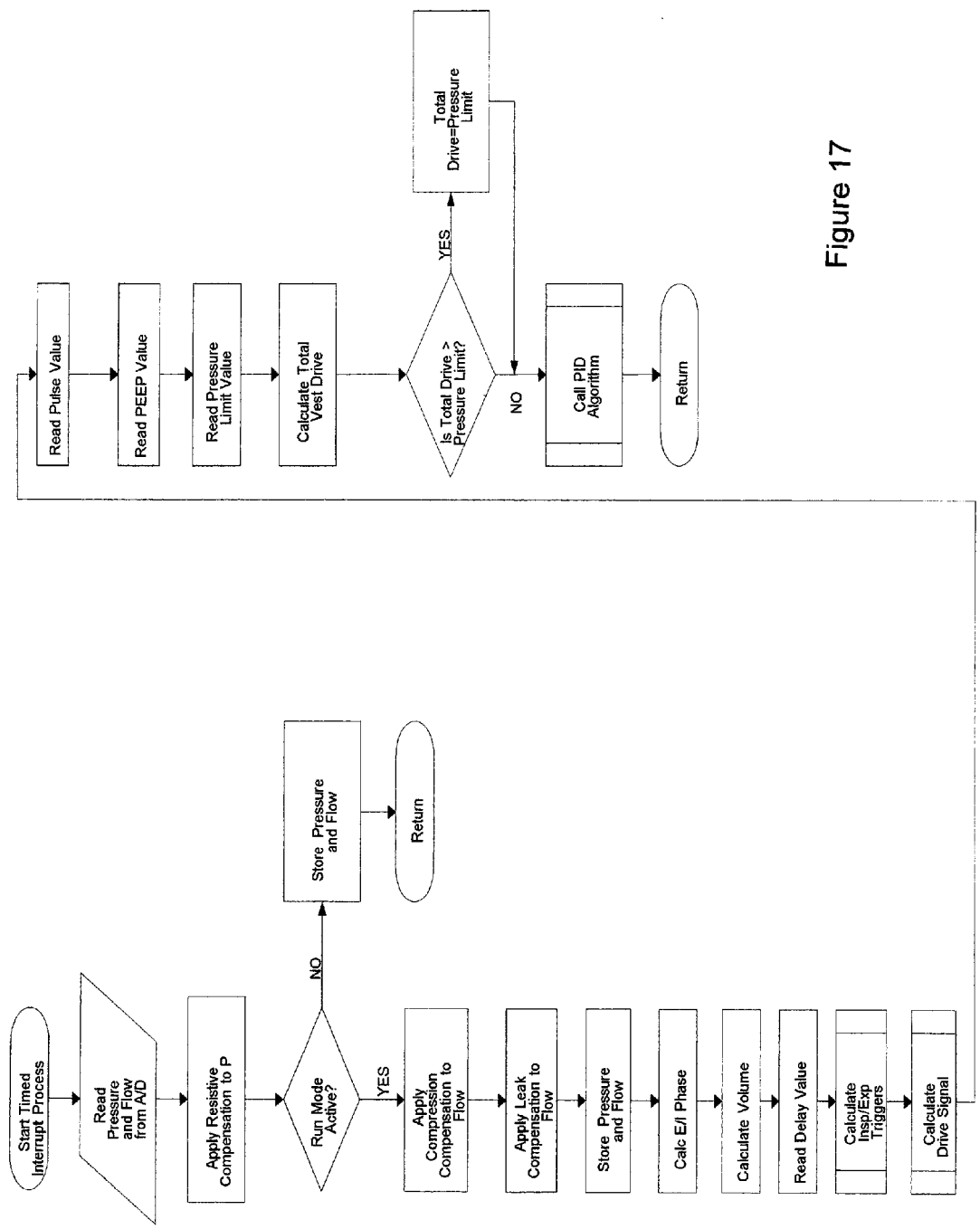
Figure 18:
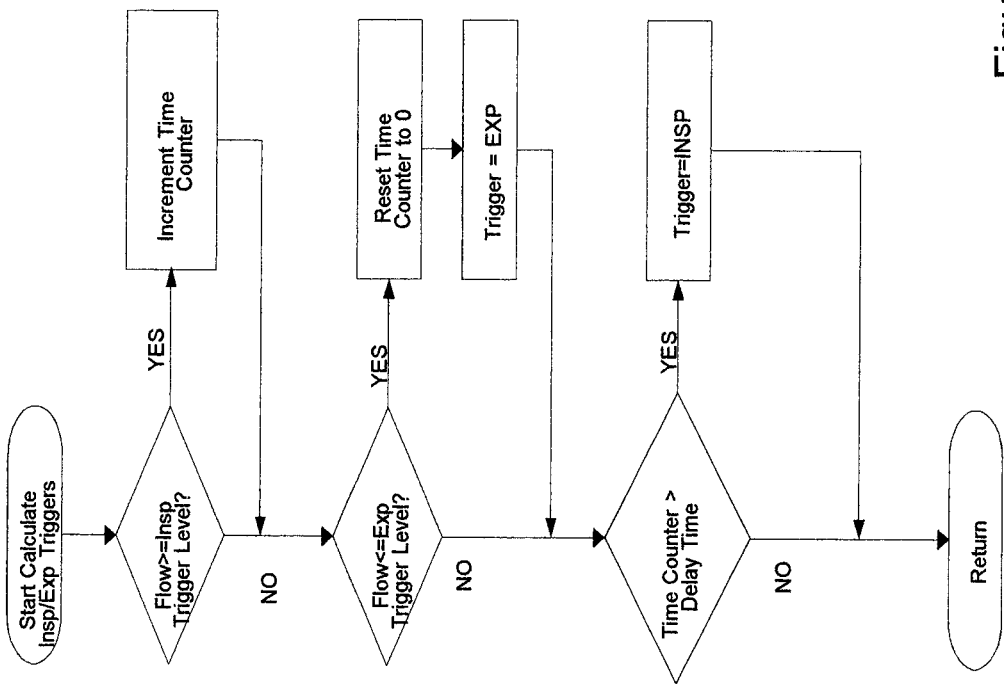
Figure 19:
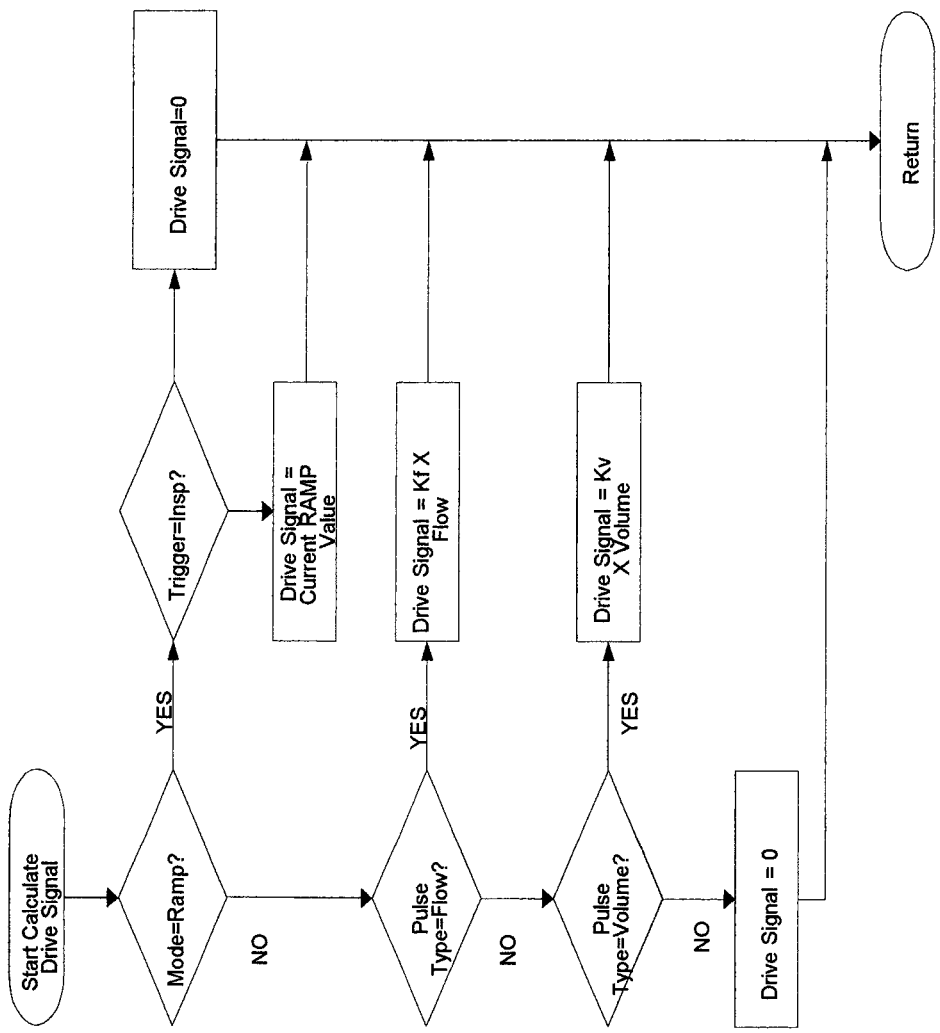
Figure 20:
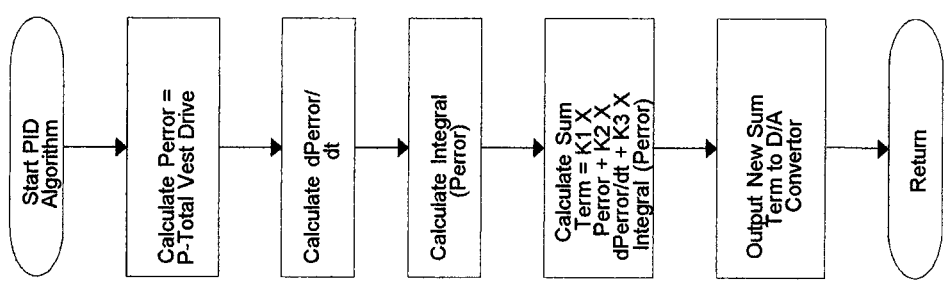

Because all functions incorporated in this preferred embodiment can be easily executed by software using very basic digital technology, implementation of the current invention using digital embodiments does not require any inventive steps and is covered by the current filing. A high level example of digital implementation of this embodiment is provided in FIG. 10. The numbers inside the various functions in this Figure refer to the Figures describing the digital implementation of the specified functions. Digital embodiments may also incorporate memory that can be downloaded at the end of a home study to establish diagnosis or response to therapy.

This preferred embodiment was developed with multitudes of functions. This was deliberate in view of the heterogeneity of sleep-related respiratory disorders and the expectation that different disorders will require different patterns of pressure application. This type of device, with a wide potential, is particularly suited to situations where one does not know a priori what function will work in a particular patient. Such a diverse device would be appropriate for research studies or in sleep laboratories to determine which function best suits a particular patient. However, once the pattern required for a given patient is determined, such a complex system would not be necessary for nightly use at home (i.e. for maintenance therapy). It is thus anticipated that devices with only limited functionality will be manufactured to suit different types of patients, with the unnecessary functions either removed or inactivated. Such reduced embodiments should clearly fall within the scope of this invention.

Most of the controls in this preferred embodiment are manually adjusted. This, again, was deliberate to facilitate experimentation with different settings using visual feedback from the response of respiratory signals as settings are changed. Ultimately, in commercial products, many or all of the adjustments that are implemented manually in this prototype can be implemented automatically through logic circuits. For example, for use in treating snoring, the amplitude and timing of pressure application can be automatically adjusted using feedback from a sound detector. For RERAs, the magnitude of applied pressure may be adjusted using a suitable signal that reflects flow limitation, and so on. Such modifications are within the scope of the current invention.

The preferred embodiment is capable of serving as a breathing monitor, for diagnostic purposes, as well as for delivery of therapy. For the diagnostic function, only a small constant pressure (PEEP) is applied (i.e. no Respiratory-related further increases). For such application, many of the functions can be removed or inactivated and the pressure required (such as 2 to 3 cmH2O) can be delivered by much smaller blowers that can be powered by batteries for a whole night's study (e.g. Sunon GB1205PHVX-8AY). It is advantageous to have both functions in the same device since once function can be used initially for diagnosis but, once the device establishes the presence of a specific abnormality through built-in algorithms, it could initiate therapy in the same night. However, it can be envisioned that some manufacturers may offer the device for diagnostic purposes only. Such stripped down devices are within the scope of this invention.

Operation:

Ideally, the device is first tested in a sleep laboratory to determine the type and magnitude of pressure application required to correct the patient's abnormality. Thereafter the desirable settings can be applied to a Therapy device to be used by the patient at home.

1. A vest of suitable size is applied to the patient and buckled. The straps (13) are adjusted to result in a moderately snug fit (not too tight). The vest is connected to the blower via the tubing (3). Pressure (18) and the output of the Summing Circuit (34) are displayed on a monitor by use of the Analog Output ports (12b).

2. Making the Leak and Compression adjustments: The patient is asked to hold his breath (close the glottis) so that lung volume remains constant during pressure ramp application. Circuit pressure is increased to a suitable level (e.g. 20 cmH$_2$O). Pressure is maintained until Vest Flow stabilizes, usually in a few seconds. The external gain control for the Leak Flow Circuit (32) is then adjusted to return the Summing Amplifier output (34) to zero. At this point the Summing Amplifier output has been leak compensated. Next, the subject is asked to hold his breath again and pressure in the circuit is increased to a suitable level (e.g. 20 cmH$_2$O). The external controls for the high pass filter (29) and Gain circuit (31) of the Compression Compensation Circuit (27) are adjusted such that the output of the Summing circuit (34) remains close to zero during the rising phase of pressure. This process may initially require several attempts but since these constants (RC of the Vest/tubing, and Compliance of the Vest) do not change much, only minor adjustments are needed thereafter. Furthermore, the compensation settings can be calculated mathematically from a single trial and adjusted automatically. Clearly, this step can be automated in commercial equipment providing this method of treatment.

Figure 21:
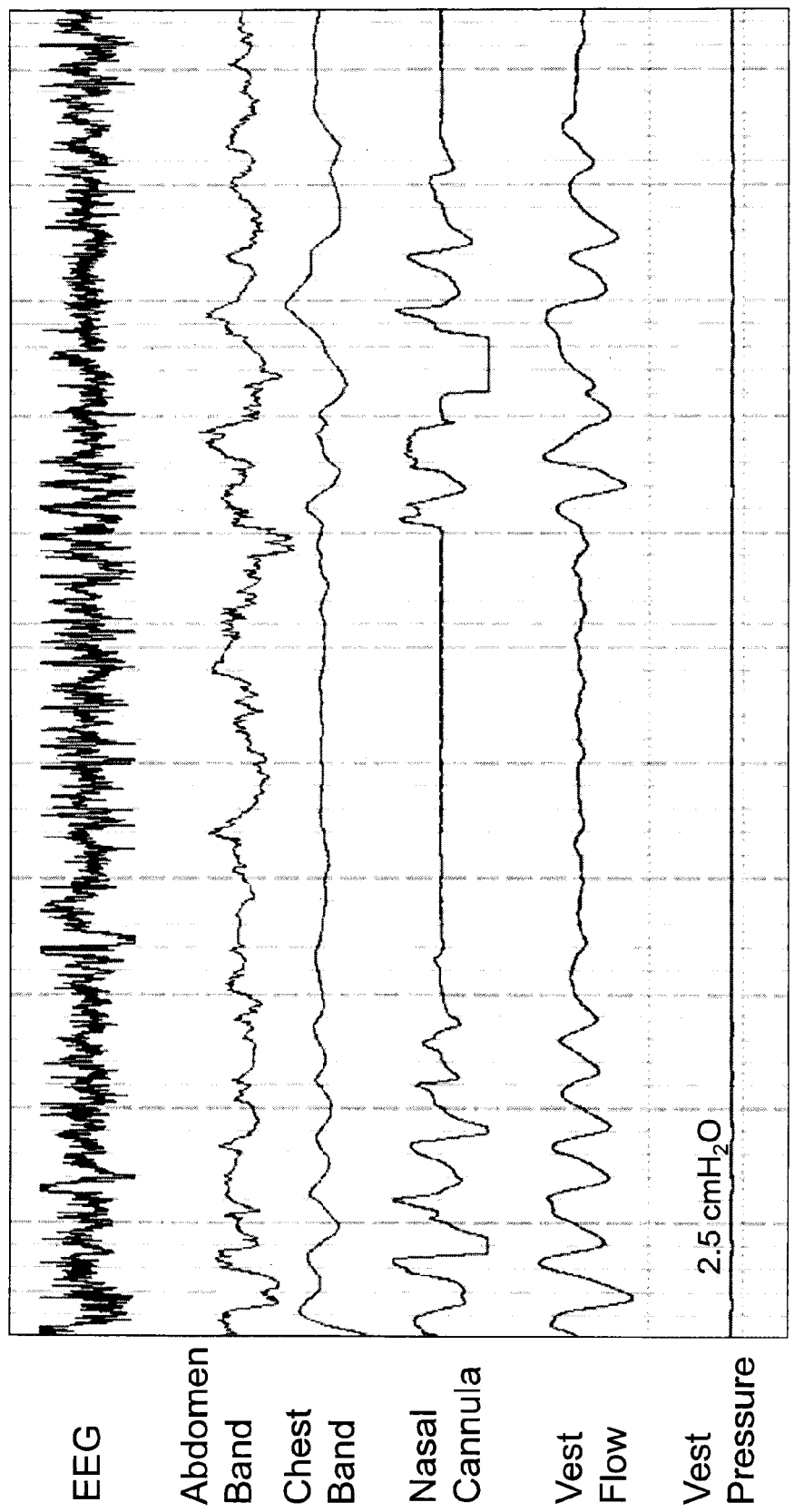
FIG. 21 shows tracings illustrating the operation of the current invention in the diagnostic mode. Note that Vest pressure is constant at a low level.

3. The patient is then free to fall asleep. The expiratory pressure is set to, say, 2 to 3 cmH$_2$O and no Respiratory-related additional pressure is applied (i.e. Rotary Switch (61) is set to "no pulse"). In this configuration the Summing Circuit Output (34) simply provides Patient flow (e.g. FIG. 21). When the patient falls asleep the Summing Circuit Output (34) can be used as the primary signal for respiratory amplitude, allowing identification of hypopneas and apneas with great precision (FIG. 21). Once the type of respiratory abnormality, if any, is determined the operator utilizes the external controls to select the type and magnitude of Respiratory-related pressure required to mitigate the abnormality. These settings can then be used in the Therapy device.

Figure 22:
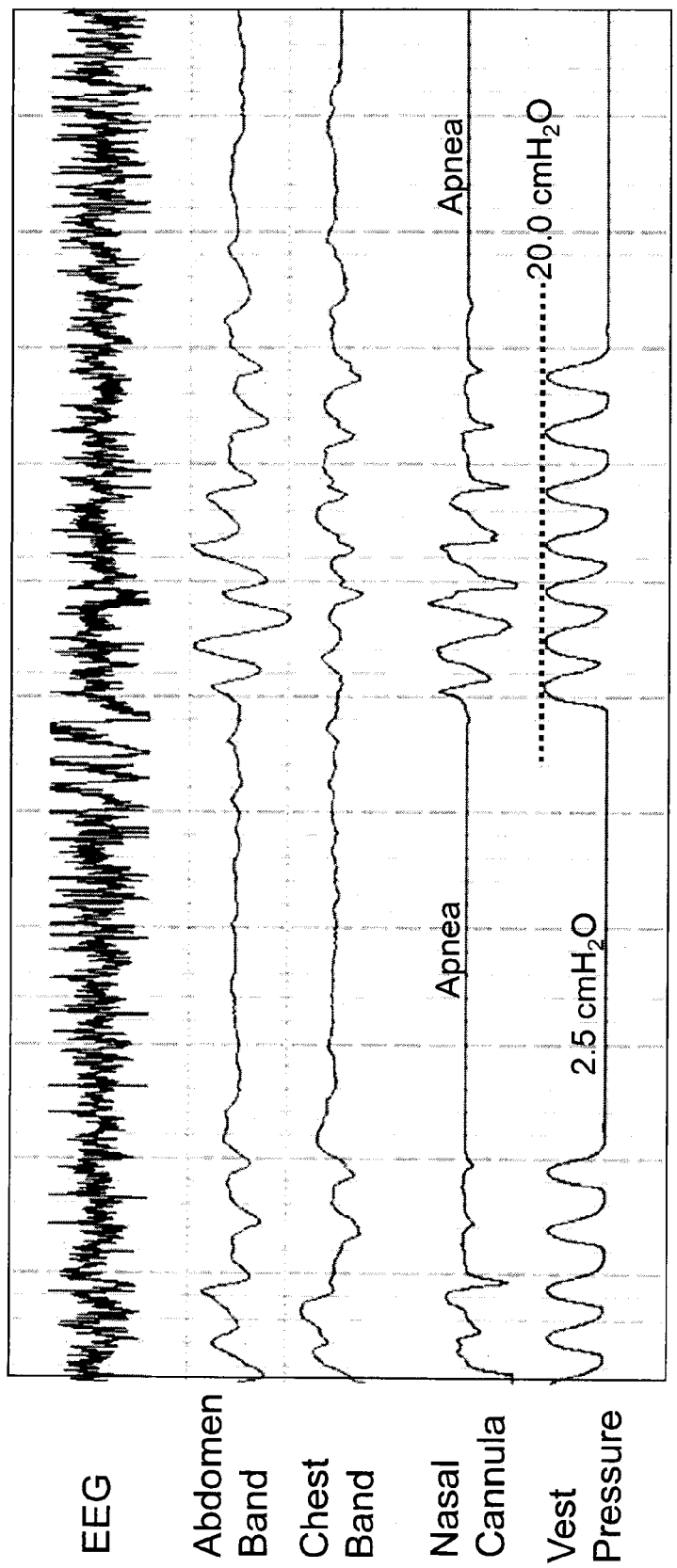
FIG. 22 shows tracings illustrating the operation of the present invention when configured to deliver Ramp pressure increases during successive inspiratory phases in the ventilator phases following apneas in order to attenuate the ventilator overshoot. In this example, the pressure ramps were triggered by an external flow input (Nasal Cannula)
Figure 23:
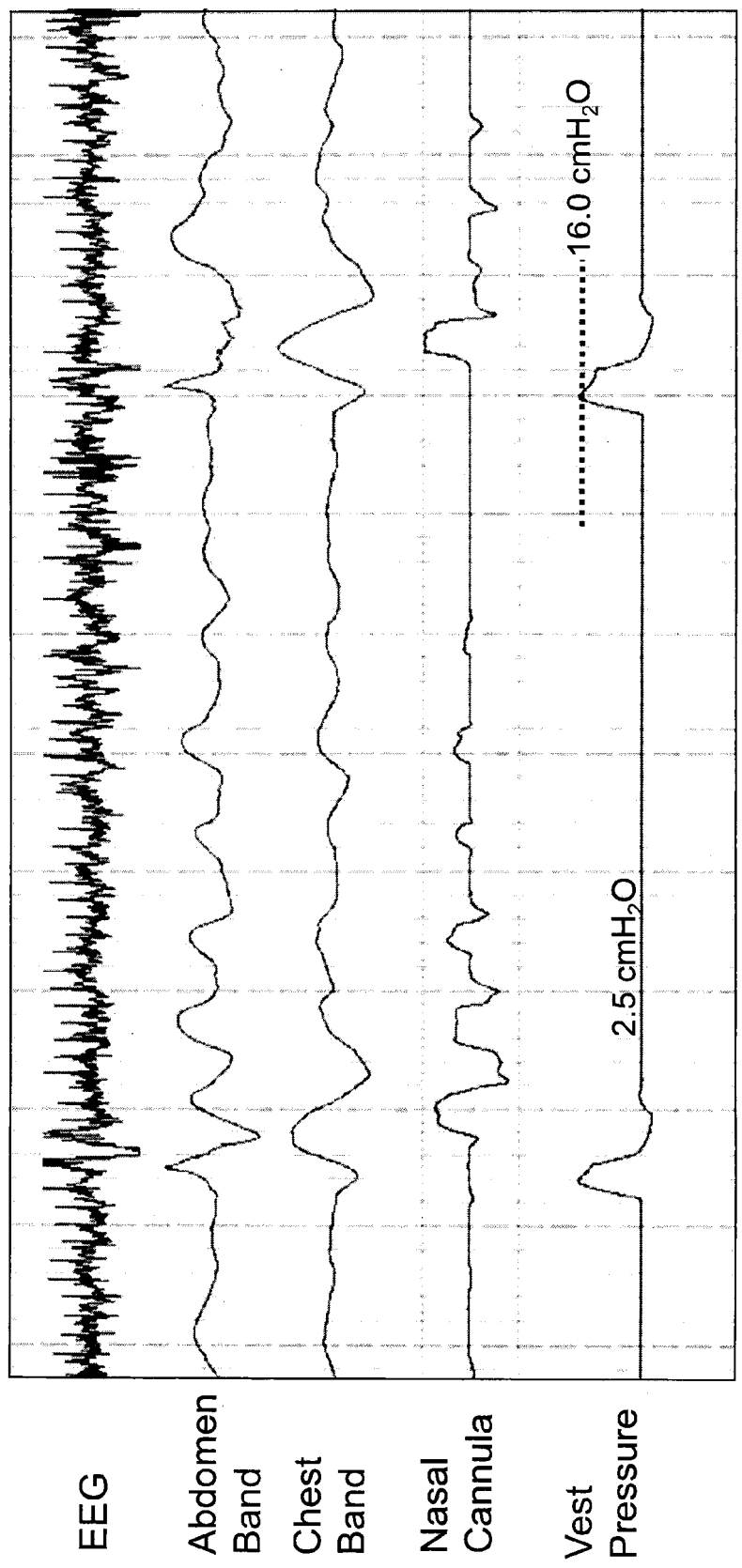
FIG. 23 shows tracings illustrating the operation of the current invention when single Ramp pressure pulses are delivered in selected exhalation phases during apneas. Note that in both cases the airway opened during the inspiration following the pulse.

Two examples of Respiratory-Related pressure applications to patients while asleep are shown in FIGS. 22 and 23. In FIG. 22, pressure ramps were applied during the inspiratory phase in successive breaths. In FIG. 23, pressure ramps were applied during the expiratory phase.

SUMMARY OF THE DISCLOSURE

In summary of this disclosure, a method and device for treating sleep apnea and related disorders, such as snoring and respiratory effort-related arousals are provided comprising:

applying an inflatable implement to the external surface of the chest and/or abdomen of a patient, said implement being capable of exerting a positive pressure to said chest and/or abdomen of said patient, causing pressure within said Vest to rise continuously to a set positive value (Continuous Pressure), and monitoring the rate of airflow into and/or out of said Vest (Vest Flow), whereby said Vest Flow is displayed or processed to obtain information about the breathing characteristics of said patient.

Optionally, increasing Vest pressure transiently above said Continuous Pressure according to specified functions that are linked to the inspiratory phase, the expiratory phase or both phases of breathing.

Modifications are possible within the scope of the invention.

The invention claimed is:

1. A method for diagnosing and/or treating sleep related disorders comprising:
    applying an inflatable implement to the external surface of the chest and/or abdomen of a patient, said inflatable implement being capable of exerting positive pressure to said chest and/or abdomen of said patient,
    causing pressure within said inflatable implement to rise to and remain substantially constant at a set positive value of low magnitude throughout the patient's breathing cycle,
    monitoring the rate of airflow into and/or out of said inflatable implement to obtain information about the breathing characteristics of said patient.

2. The method of claim 1 wherein said inflatable implement is an inflatable vest or cuff.

3. The method of claim 1 wherein the inflatable implement compresses only the upper part of the torso of the patient.

4. The method of claim 1 including identifying the inspiratory phase of breathing using the obtained information.

5. The method of claim 1 wherein the sleep related disorders comprise sleep apnea, snoring and respiratory effort-related arousals.

6. The method of claim 1 further comprising displaying and/or processing the rate of airflow.

7. A device for diagnosing and/or treating sleep related disorders comprising:
    an inflatable implement that can be applied to the external surface of the chest and/or abdomen of a patient, said inflatable implement being capable of exerting positive pressure to said chest and/or abdomen of said patient,
    a positive pressure source,
    tubing connecting said positive pressure source to said inflatable implement,
    electrical and/or digital circuitry that controls said pressure source and is capable of causing pressure within said inflatable implement to rise to and remain substantially constant at a set positive value of low magnitude throughout the patient's breathing cycle, and
    circuitry to monitor the rate of airflow into and/or out of said inflatable implement to obtain information about the breathing characteristics of said patient.

8. The device of claim 7 wherein said inflatable implement is an inflatable vest or cuff.

9. The device of claim 7 wherein the inflatable implement is configured to compress only the upper part of the torso of the patient.

10. The device of claim 7 including means to identify the inspiratory phase of breathing using the obtained information.

11. The device of claim 7 including circuitry that measures flow and volume changes or receives flow and volume information from an independent source.

12. The device of claim 7 further comprising circuitry to process said rate of airflow.

13. The device of claim 7 further comprising a display device to display said rate of airflow.

14. A device for diagnosing and/or treating sleep related disorders comprising:
    an inflatable implement that can be applied to the external surface of the chest and/or abdomen of a patient,
    a positive pressure source,
    tubing connecting said positive pressure source to said inflatable implement,
    electrical and/or digital circuitry that controls said pressure source and is capable of causing pressure within said inflatable implement to remain substantially constant at a set positive value of low magnitude to cause said inflatable implement to exert positive pressure to said chest and/or abdomen of said patient throughout the patient's breathing cycle, and
    circuitry to monitor the rate of airflow into and/or out of said inflatable implement, said rate of airflow reflecting spontaneous changes in the breathing of said patient.

15. The device of claim 14 wherein said inflatable implement is an inflatable vest or cuff.

16. The device of claim 14 wherein the inflatable implement is configured to compress only the upper part of the torso of the patient.

17. The device of claim 14 including means to process the rate of airflow to identify the inspiratory phase of breathing.

18. The device of claim 14 including circuitry that measures flow and volume changes or receives flow and volume information from an independent source.

* * * * *